(12) United States Patent
Llewellyn et al.

(10) Patent No.: US 9,243,260 B2
(45) Date of Patent: Jan. 26, 2016

(54) FIBER SELECTIVE PROMOTERS

(75) Inventors: Danny Llewellyn, O'Connor (AU); Frank Meulewaeter, Merelbeke (BE)

(73) Assignees: Bayer CropScience NV, Diegem (BE); Commonwealth Scientific and Industrial Research Organization, Campbell, Austrialian Capital Territory (AU)

( * ) Notice: Subject to any disclaimer, the term of this patent is extended or adjusted under 35 U.S.C. 154(b) by 227 days.

(21) Appl. No.: 13/977,749

(22) PCT Filed: Dec. 21, 2011

(86) PCT No.: PCT/EP2011/073627
§ 371 (c)(1),
(2), (4) Date: Jul. 1, 2013

(87) PCT Pub. No.: WO2012/093032
PCT Pub. Date: Jul. 12, 2012

(65) Prior Publication Data
US 2013/0276170 A1    Oct. 17, 2013

Related U.S. Application Data

(60) Provisional application No. 61/429,615, filed on Jan. 4, 2011.

(30) Foreign Application Priority Data

Jan. 5, 2011 (EP) .................................... 11075002

(51) Int. Cl.
C12N 15/82 (2006.01)

(52) U.S. Cl.
CPC ........ *C12N 15/8242* (2013.01); *C12N 15/8222* (2013.01)

(58) Field of Classification Search
None
See application file for complete search history.

(56) References Cited

U.S. PATENT DOCUMENTS

| | | |
|---|---|---|
| 4,757,011 A | 7/1988 | Chaleff et al. |
| 4,769,061 A | 9/1988 | Comai |
| 4,940,835 A | 7/1990 | Shah et al. |
| 4,971,908 A | 11/1990 | Kishore et al. |
| 5,004,863 A | 4/1991 | Umbeck |
| 5,593,874 A | 1/1997 | Brown et al. |
| 5,641,876 A | 6/1997 | McElroy et al. |
| 5,659,122 A | 8/1997 | Austin |
| 6,096,950 A | 8/2000 | John |
| 6,483,013 B1 | 11/2002 | Reynaerts et al. |
| 6,566,587 B1 | 5/2003 | Lebrun et al. |
| 7,172,881 B2 | 2/2007 | Huang et al. |

| | | | |
|---|---|---|---|
| 2003/0221218 A1* | 11/2003 | Wilkins | 800/284 |
| 2009/0293146 A1* | 11/2009 | Ayal et al. | 800/278 |
| 2011/0191912 A1* | 8/2011 | Alexandrov et al. | 800/298 |

FOREIGN PATENT DOCUMENTS

| | | |
|---|---|---|
| WO | 9012107 | 10/1990 |
| WO | 9215675 | 9/1992 |
| WO | 9640924 | 12/1996 |
| WO | WO 96/40924 | * 12/1996 |
| WO | 0071733 | 11/2000 |
| WO | 03052108 | 6/2003 |
| WO | 2005098004 | 10/2005 |
| WO | 2007039317 | 4/2007 |
| WO | 2010015423 | 2/2010 |
| WO | 2012093032 | 7/2012 |
| WO | WO 2014/184196 AI | * 11/2014 |

OTHER PUBLICATIONS

Donald & Cashmore, EMBO J 9:1717-26 (1990).*
Kim et al., Plant Mol Biol 24:105-17 (1994).*
Dolferus et al., Plant Physiol 105:1075-87 (1994).*
Fourgoux-Nicol et al., Plant Mol Biol 40:857-72 (1999).*
Potenza et al., In Vitro Cell Dev Biol Plant 40:1-22 (2004).*
Wahl et al. (Meth Enzymol 152:399-407 (1987).*
Din and Yarden, 1994, The Neurospora crassa chs-2 gene encodes a non-essential chitin synthase, Microbiology 140: 2189-2197.
Jefferson et al., 1987, GUS fusions: ,B-glucuronidase as a sensitive and versatile gene fusion marker in higher plants, EMBO J. 6: 3901-3907.
Ji et al., 1003, Isolation and analyses of genes preferentially expressed during early cotton fiber development by subtractive PCR and cDNA array, Nucleic Acids Res. 31: 2534-2543.
Murray et al., 1999, Expression of the Talaromyces flavus glucose oxidase gene in cotton and tobacco reduces fungal infection, but is also phytotoxic, Mol. Breed, 5: 219-232.
Needleman and WUNSCH, 1970, A General Method Applicable to the Search for Similarities in the Amino Acid Sequence of Two Protiens, J. Mol. Biol. 48: 443-453.
Orford and Timmis, 1997, Abundant mRNAs specific to the developing cotton fibre, Theor Appl Genet 94: 909-918.
Orford et al., 1999, Characterisation of a cotton gene expressed late in fibre cell elongation, Theor Appl Genet 98: 757-764.
Pagny et al., 2003, Structural requirements for Arabidopsis b1,2-xylosyltransferase activity and targeting to the Golgi, The Plant Journal, 30: 189-203.
Pearson and Lipman, 1988, Improved tools for biological sequence comparison, Proc. Natl. Acad. Sci. 85: 2444-2448.
Schunmann et al., 2003, A Suite of Novel Promoters and Terminators for Plant Biotechnology, Funct Plant Biol 30: 443-452.
Thompson et al., 1987, Characterization of the herbicide-resistance gene bar from Streptomyces hygroscopicus, EMBO Journal 6: 2519-2523.
International Search Report for PCT Application No. PCT/EP2011/073627 dated Dec. 21, 2011.

* cited by examiner

*Primary Examiner* — David H Kruse
*Assistant Examiner* — Russell Boggs

(57) ABSTRACT

The present invention relates to materials and methods for the expression of a gene of interest selectively in cotton fibers. In particular, the invention provides an expression cassette for regulating fiber-selective expression in plants.

14 Claims, 14 Drawing Sheets

FS18-GUS Transformant T420-48

Young leaf

Petiole 10 dpa ovules 20 dpa ovules

Root

Stem

Figure 5E

| | T420-24 plant 14 | T420-24 plant 15 | T420-31 plant 29 | T420-31 plant 44 | T420-37 plant 76 | T420-37 plant 87 | T420-48 plant 55 | T420-48 plant 57 | Mean all plants | SD | SE |
|---|---|---|---|---|---|---|---|---|---|---|---|
| 0dpa | 0,013 | 0,226 | 0,007 | 0,051 | 0,069 | 0,072 | 0,013 | 0,026 | 0,060 | 0,072 | 0,026 |
| 10dpa | 0,100 | 0,682 | 0,049 | 0,016 | 0,187 | 0,062 | 0,040 | 0,039 | 0,147 | 0,223 | 0,080 |
| 20dpa | 0,337 | 0,360 | 0,043 | 0,085 | 0,548 | 0,404 | 0,293 | 0,200 | 0,284 | 0,168 | 0,060 |
| 30dpa | 1,000 | 1,001 | 1,000 | 1,000 | 1,000 | 1,000 | 1,000 | 1,000 | 1,000 | 0,000 | 0,000 |
| 10dpa Bollcoat | 1,185 | 0,129 | 0,329 | 0,241 | 0,444 | 0,478 | 0,483 | 0,113 | 0,425 | 0,341 | 0,122 |
| Bract | 0,570 | 0,154 | 0,037 | 0,116 | 0,425 | 0,062 | 0,071 | 0,067 | 0,188 | 0,198 | 0,071 |
| Leaf | 2,858 | 0,081 | 0,054 | 0,118 | 1,307 | 0,193 | 0,265 | 0,195 | 0,634 | 0,988 | 0,353 |
| Petal | 0,031 | 0,135 | 0,012 | 0,012 | 0,112 | 0,019 | 0,004 | 0,008 | 0,041 | 0,052 | 0,018 |
| Root | 0,000 | 0,001 | 0,005 | 0,001 | 0,010 | 0,013 | 0,001 | 0,002 | 0,004 | 0,005 | 0,002 |
| Stamen | 0,106 | 0,190 | 0,019 | 0,046 | 0,115 | 0,056 | 0,025 | 0,057 | 0,077 | 0,057 | 0,020 |
| Stem | 0,776 | 0,318 | 0,024 | 0,049 | 0,030 | 0,177 | 0,089 | 0,047 | 0,189 | 0,257 | 0,092 |
| Stigma | 0,398 | 0,191 | 0,072 | 0,099 | 0,183 | 0,070 | 0,103 | 0,040 | 0,144 | 0,116 | 0,041 |
| Cotyledon | nd | 0,018 | nd | 0,084 | nd | 0,086 | 0,116 | nd | 0,076 | 0,041 | 0,021 |

Figure 6E

| | T427-26-1 plant 16 | T427-26-1 plant 7 | T427-5 plant 25 | T427-5 plant 41 | T427-31 plant 78 | T427-31 plant 82 | T427-6 plant 58 | T427-6 plant 67 | Mean all plants | SD | SE |
|---|---|---|---|---|---|---|---|---|---|---|---|
| 0dpa | 0,210 | 0,041 | 0,061 | 0,092 | 0,085 | 0,052 | 0,155 | 0,141 | 0,105 | 0,059 | 0,021 |
| 10dpa | 0,235 | 0,115 | 0,099 | 0,080 | 0,326 | 0,132 | 0,217 | 0,148 | 0,169 | 0,083 | 0,030 |
| 20dpa | 0,229 | 0,311 | 0,155 | 0,317 | 0,173 | 0,185 | 0,487 | 0,711 | 0,321 | 0,191 | 0,068 |
| 30dpa | 1,000 | 1,000 | 1,001 | 1,001 | 1,000 | 1,000 | 1,000 | 1,000 | 1,000 | 0,000 | 0,000 |
| 10 dpa Bollcoat | 0,293 | 0,166 | 0,048 | 0,089 | 0,626 | 0,521 | 0,207 | 0,667 | 0,327 | 0,244 | 0,086 |
| Bract | 0,083 | 0,042 | 0,176 | 0,055 | 0,283 | 0,381 | 0,375 | 0,075 | 0,184 | 0,143 | 0,051 |
| Leaf | 0,310 | 0,234 | 0,182 | 0,175 | 0,207 | 0,084 | 0,483 | 0,255 | 0,241 | 0,118 | 0,042 |
| Petal | 0,008 | 0,008 | 0,013 | 0,006 | 0,015 | 0,004 | 0,008 | 0,007 | 0,009 | 0,003 | 0,001 |
| Root | 0,003 | 0,006 | 0,005 | 0,009 | 0,010 | 0,012 | 0,008 | 0,010 | 0,008 | 0,003 | 0,001 |
| Stamen | 0,039 | 0,013 | 0,023 | 0,221 | 0,054 | 0,024 | 0,068 | 0,096 | 0,067 | 0,068 | 0,024 |
| Stem | 0,076 | 0,448 | 0,114 | 0,073 | 0,086 | 0,015 | 0,173 | 0,141 | 0,141 | 0,133 | 0,047 |
| Stigma | 0,082 | 0,587 | 0,193 | 0,027 | 0,084 | 0,023 | 0,353 | 0,089 | 0,180 | 0,197 | 0,070 |
| Cotyledon | nd | 0,044 | 0,058 | nd | 0,121 | nd | 0,135 | nd | 0,089 | 0,045 | 0,022 |

FIBER SELECTIVE PROMOTERS

CROSS-REFERENCE TO RELATED APPLICATIONS

This application is a §371 U.S. National Stage of International Application No. PCT/EP2011/073627, filed Dec. 21, 2011, which claims the benefit of European Patent Application Serial No. 11075002.3, filed Jan. 5, 2011 and U.S. Patent Application Ser. No. 61/429,615, filed Jan. 4, 2011, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "bcs11_2001_wo1_ST25.txt", created on Dec. 21, 2011, and having a size of 22,000 bytes and is filed concurrently with the specification. The sequence listing contained in this ASCII formatted document is part of the specification and is herein incorporated by reference in its entirety.

FIELD OF THE INVENTION

The present invention relates to materials and methods for the expression of a gene of interest preferentially or selectively in fibers of plants, such as cotton plants. In particular, the invention provides an expression cassette for regulating fiber-preferential or fiber-selective expression in cotton plants.

INTRODUCTION TO THE INVENTION

Cotton (*Gossypium* spp.) is the world's most important natural textile fiber and is also a significant oilseed crop. Cotton production provides income for approximately 100 million families, and approximately 150 countries are involved in cotton import and export. Its economic impact is estimated to be approximately $500 billion/year worldwide. World consumption of cotton fiber is approximately 115 million bales or approximately 27 million metric tons per year (National Cotton Council, www.cotton.org/, 2006). The genus *Gossypium* is relatively complex and includes approximately 45 diploid (2n=2x=26) and five tetraploid (2n=4x=52) species, all exhibiting disomic patterns of inheritance. Diploid species (2n=26) fall into eight genomic groups (A-G, and K). The African clade, comprising the A, B, E, and F genomes, occurs naturally in Africa and Asia, while the D genome clade is indigenous to the Americas. A third diploid clade, including C, G, and K, is found in Australia. All 52 chromosome species, including *Gossypium hirsutum* and *Gossypium barbadense*, are classic natural allotetraploids that arose in the New World from interspecific hybridization between an A genome-like ancestral African species and a D genome-like American species. The closest extant relatives of the original tetraploid progenitors are the A genome species *Gossypium herbaceum* (A1) and *Gossypium arboreum* (A2) and the D genome species *Gossypium raimondii* (D5) 'Ulbrich'. Polyploidization is estimated to have occurred 1 to 2 million years ago, giving rise to five extant allotetraploid species. Interestingly, the A genome species produce spinnable fiber and are cultivated on a limited scale, whereas the D genome species do not. More than 95% of the annual cotton crop worldwide is *G. hirsutum*, Upland or American cotton, and the extra-long staple or Pima cotton (*G. barbadense*) accounts for less than 2% (National Cotton Council, www.cotton.org/, 2006). Understanding the contribution of the A and D subgenomes to gene expression in the allotetraploids may facilitate improving fiber traits but unfortunately most of the sequence information of cotton is currently lacking and decoding cotton genomes will be a foundation for improving understanding of the functional and agronomic significance of polyploidy and genome size variation within the *Gossypium* genus.

Each cotton fiber is a differentiated single epidermal cell of the ovule. Approximately half a million fibers are produced per cotton boll, some forming fuzz and some forming lint. Initiation of an epidermal cell into fiber requires a change in cell fate, which is a fundamental biological process involving genetic, physiological and developmental "switches". Genetic mutations, polyploidy, pollination/fertilization, and hormonal regulation can affect the number of cells developing into fibers or alter fiber cell properties (fuzz vs. lint). However, it is unclear how these factors control gene expression changes that orchestrate the pattern and tempo in early stages of fiber development.

In contrast, the morphological development of cotton fibers is well documented in the art. Cotton fibers undergo four overlapping developmental stages: fiber cell initiation, elongation, secondary wall biosynthesis, and maturation. Fiber initiation is a rapid process. The white fluffy fibers begin to develop immediately after anthesis and continue up to 3 days post-anthesis (DPA), which is followed by fiber cell elongation (until 20 DPA). Secondary wall biosynthesis initiates around 15 dpa and continues to 35 DPA, followed by a maturation process until 45-60 DPA. Cotton fibers are derived from ovular epidermal cells (maternal tissues). However, only ~25-30% of the epidermal cells differentiate into the commercially important lint fibers. The majority of cells does not differentiate into fibers or develop into short fibers or fuzz. For the cells committed to fiber development, cell initiation and elongation are nearly synchronous on each ovule, indicating that changes in gene expression are orchestrated during fiber differentiation and development through intercellular signaling and/or timing mechanisms.

Genetic improvement of fiber production and processing should ensure that this natural renewable product becomes competitive with petroleum-derived synthetic fibers.

Studies that identify genes that are under tissue-selective and developmental regulation are important in understanding the roles of proteins in fiber development and cell-wall architecture. In addition, such genes and especially their regulatory elements and promoters provide important tools for fiber modification through genetic engineering. In many instances, it would be desirable for a transgene to be developmentally regulated to have exclusive or specific expression in fiber cells at a defined developmental stage. This regulation can be most expeditiously accomplished by a promoter capable of fiber-specific expression.

Useful promoters drive gene expression preferentially or selectively and strongly in fibers, i.e. strongly and continuously from the fiber elongation phase through initiation of secondary wall deposition towards its termination. The initiation of secondary wall deposition is defined as the time when the dry weight/unit length of a cotton fiber begins to increase or when the dry weight/unit surface area of any cell begins to increase via synthesis of new wall material containing more than 40% (w/w) of cellulose. In the case of cotton fiber of *G. hirsutum* L., this is expected to occur between 14-17 DPA when cotton plants are grown under typical conditions in the greenhouse or the field (day temperature of

SUMMARY OF THE INVENTION

Figure 1:
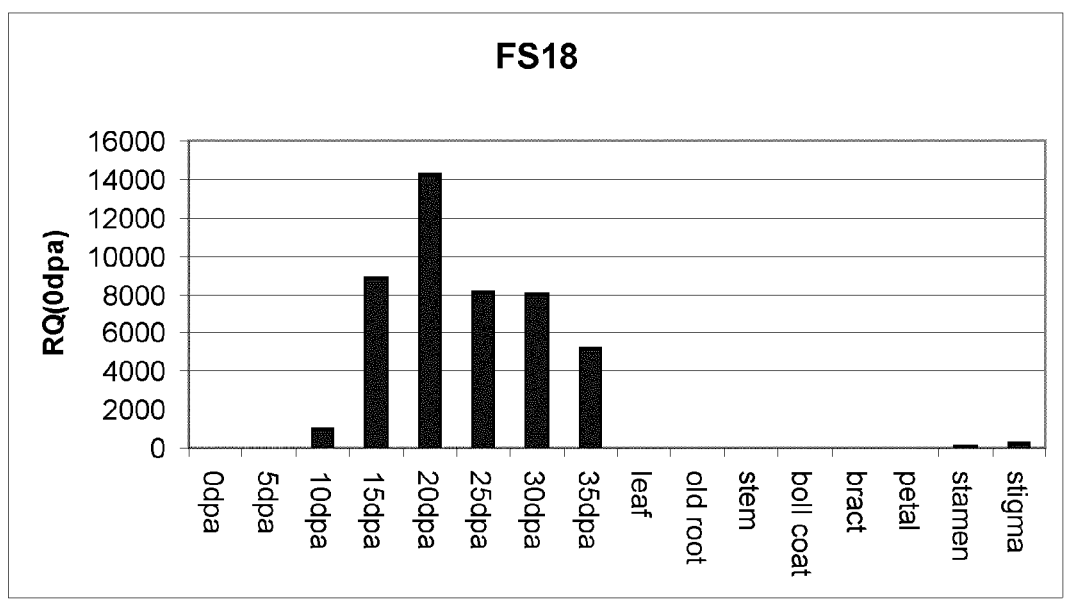
FIG. 1: Relative expression by quantitative RT-PCR of FS18 in different cotton tissues using the cotton RNA helicase gene as a reference. Values are the average of four technical replicates. FS18 is expressed throughout fiber development both in the elongation and cell wall thickening stages.

The present invention relates to isolated nucleic acid molecules from cotton which are capable of directing expression or transcription of an operably linked DNA region, such as a DNA region encoding a biologically active RNA preferentially or selectively in fibers of a fiber containing or producing plant such as cotton. These chimeric genes are furthermore expressed in fibers during elongation and secondary wall deposition.

Thus, the invention relates to chimeric DNA constructs each comprising a DNA promoter operably linked 5' to a second DNA, which encodes a biologically active RNA, and a 3' regulatory region operably linked to the second DNA. The DNA construct can be incorporated in an expression system, a vector, a host cell, a plant, or a plant seed.

Another aspect of the present invention relates to isolated DNA promoters suitable for inducing expression of a protein encoded by a second DNA operably associated with the DNA promoter. The DNA promoters are isolated from cotton and drive expression preferentially or selectively in fibers during elongation and secondary wall deposition.

A further aspect of the present invention is directed to a method of expressing a gene preferentially or selectively in fibers during elongation and secondary wall deposition in a plant comprising transforming a plant with the DNA construct comprising an isolated DNA promoter of the present invention.

In addition, a promoter of a gene that is expressed preferentially or selectively in fibers during elongation and secondary wall deposition of normal plants can be valuable for genetic engineering of fiber to achieve: (1) improved agricultural productivity under normal and stressed conditions and (2) improved fiber properties that depend on modification during secondary wall deposition. The promoters disclosed in the present invention allow these goals to be met while avoiding or minimizing pleiotropic effects on plant growth and development or other stages of fiber development that could reduce the benefit of the targeted effects.

In one embodiment the invention provides a fiber cell preferential or selective promoter selected from the following group of sequences: i) a nucleotide sequence comprising the nucleotide sequence of SEQ ID NO: 1 or SEQ ID NO: 2, ii) a nucleotide sequence comprising a nucleotide sequence having at least 90%, particularly at least 95% sequence identity with SEQ ID NO: 1 or SEQ ID NO: 2, iii) a nucleotide sequence comprising an about 500 bp to an about 1375 bp DNA fragment hybridizing under stringent conditions with a nucleotide sequence mentioned under i) or ii).

In another embodiment the invention provides for a chimeric gene comprising the following operably linked DNA regions i) a fiber cell selective or preferential promoter according to: i) a nucleotide sequence comprising the nucleotide sequence of SEQ ID NO: 1 or SEQ ID NO: 2 or ii) a nucleotide sequence comprising a nucleotide sequence having at least 90%, particularly at least 95% sequence identity with SEQ ID NO: 1 or SEQ ID NO: 2 or iii) a nucleotide sequence comprising an about 500 bp to an about 1375 bp DNA fragment hybridizing under stringent conditions with a nucleotide sequence mentioned under i) or ii) and b) a heterologous DNA region encoding a biologically active RNA of interest; and c) optionally a transcription termination and polyadenylation signal.

In a particular embodiment the chimeric gene comprises a biologically active RNA which encodes a protein of interest.

In another particular embodiment the chimeric gene the biologically active RNA is an inhibitory RNA such as a sense (cosuppression) RNA, antisense RNA, ribozyme, microRNA, double stranded hairpin RNA.

In yet another embodiment the invention provides a recombinant vector comprising a chimeric gene described herein before.

In another embodiment the invention provides a plant cell comprising a chimeric gene as described herein before.

In another embodiment the invention provides a plant comprising in its cells a chimeric gene as described herein before. The plant may have altered fiber, wherein said fiber is altered in composition, length or strength.

In a specific embodiment the plant of the invention comprising in its cells a chimeric gene of the invention is a cotton plant.

In another embodiment the invention provides a seed of a plant as described herein before.

In yet another embodiment the invention provides altered fibers of plants of harvested from plants according to the invention.

In another embodiment the invention provides a method for expressing a biologically active RNA preferentially or selectively in a fiber cell of a fiber producing plant, such as a cotton plant, said method comprising providing the cells of said plants with a chimeric gene as described herein before and growing said plants.

In a specific embodiment of the method for expressing a biologically active RNA in a fiber cell of a fiber producing plant, said plant is a cotton plant.

In another embodiment the invention provides the use of a fiber-preferential or selective promoter of the invention for preferential or selective expression of a biologically active RNA in fiber cells of a fiber-producing plant such as a cotton plant.

DETAILED DESCRIPTION OF THE INVENTION

The present invention provides promoters and expression cassettes capable of transcribing a heterologous nucleic acid sequence in a fiber, particularly transcription starts at the fiber elongation stage throughout the secondary cell wall stage of the fiber, more particularly in a cotton fiber, and methods of modifying, producing, and using the same in plants, particularly cotton plants. The present invention also provides compositions, transformed host cells, such as plants, containing an expression cassette comprising these fiber-selective promoters. The nucleotide sequence depicted in SEQ ID NO: 1 represents the nucleotide sequence of the promoter of the FS18 gene of *Gossypium hirsutum* related to other plant non-specific lipid transfer proteins. The nucleotide sequence depicted in SEQ ID NO: 2 represents the nucleotide sequence of the promoter of the proline rich protein gene nominally designated the SCW-PRP gene of *Gossypium hirsutum*.

In one embodiment the invention provides a fiber-preferential or fiber-selective promoter having the nucleotide sequence of SEQ ID NO: 1 from nucleotide position 1 to nucleotide position 1375 for use in an expression cassette. In a particular embodiment said fiber-preferential or fiber-selective promoter has the nucleotide sequence of SEQ ID NO: 1 from nucleotide position 500 to nucleotide position 1375. In yet another particular embodiment said fiber-preferential or fiber-selective promoter has the nucleotide sequence of SEQ ID NO: 1 from nucleotide position 700 to nucleotide position 1375. SEQ ID NO: 1 depicts the region upstream (i.e. located 5' upstream of) from the codon coding for the first amino acid of the FS18 protein. Such a promoter region may be at least about 300 to about 400 to about 500 bp, at least about 1000 bp, at least about 1100 bp, at least about 1300 bp upstream of the start codon of the FS18 gene.

In another embodiment the invention provides a fiber-preferential or fiber-selective promoter having the nucleotide sequence of SEQ ID NO: 2 from nucleotide position 1 to nucleotide position 1378 for use in an expression cassette. In a particular embodiment said fiber-preferential or fiber-selective promoter has the nucleotide sequence of SEQ ID NO: 2 from nucleotide position 500 to nucleotide position 1378. In yet another particular embodiment said fiber-preferential or fiber-selective promoter has the nucleotide sequence of SEQ ID NO: 2 from nucleotide position 700 to nucleotide position 1378. SEQ ID NO: 2 depicts the region upstream (i.e. located 5' upstream of) from the codon coding for the first amino acid of the SCW-PRP protein. Such a promoter region may be at least about 300 to about 400 to about 500 bp, at least about 600 bp, at least about 700 bp, at least about 800 bp, at least about 900 bp upstream of the start codon of the SCW-PRP gene.

Thus the invention provides a fiber cell preferential or selective promoter selected from the following group of sequences: i) a nucleotide sequence comprising the nucleotide sequence of SEQ ID NO: 1 or SEQ ID NO: 2, ii) a nucleotide sequence comprising a nucleotide sequence having at least 90%, particularly at least 95% sequence identity with SEQ ID NO: 1 or SEQ ID NO: 2, iii) a nucleotide sequence comprising an about 300 bp to an about 1300 bp DNA fragment hybridizing under stringent conditions with a nucleotide sequence mentioned under i) or ii).

The fiber-preferential or fiber-selective promoters according to the invention may also be comprised in a larger DNA molecule.

In a particular embodiment the fiber cell selective or preferential promoter is a promoter active during the fiber elongation stage till the end of the secondary wall synthesis phase of the fiber.

The phrases "DNA", "DNA sequence," "nucleic acid sequence," and "nucleic acid molecule" refer to a physical structure comprising an orderly arrangement of nucleotides. The DNA sequence or nucleotide sequence may be contained within a larger nucleotide molecule, vector, or the like. In addition, the orderly arrangement of nucleic acids in these sequences may be depicted in the form of a sequence listing, figure, table, electronic medium, or the like. The term "expression" refers to the transcription of a gene to produce the corresponding RNA. It is understood that the RNA which is produced is a biologically active RNA. In a particular embodiment said biologically active RNA is mRNA and translation of this mRNA produces the corresponding gene product (i.e., a peptide, polypeptide, or protein). In another particular embodiment the heterologous nucleic acid, operably linked to the promoters of the invention, may also code for a ribozyme, antisense RNA, sense RNA, double stranded RNA or synthetic or natural microRNA molecules, according to rules well known in the art, to downregulate the expression of other genes comprised within the fiber or even of genes present within a pathogen or pest that feeds upon the fibers of the transgenic plant.

The term "protein" interchangeably used with the term "polypeptide" as used herein describes a group of molecules consisting of more than 30 amino acids, whereas the term "peptide" describes molecules consisting of up to 30 amino acids. Proteins and peptides may further form dimers, trimers and higher oligomers, i.e. consisting of more than one (poly) peptide molecule. Protein or peptide molecules forming such dimers, trimers etc. may be identical or non-identical. The corresponding higher order structures are, consequently, termed homo- or heterodimers, homo- or heterotrimers etc. The terms "protein" and "peptide" also refer to naturally modified proteins or peptides wherein the modification is effected e.g. by glycosylation, acetylation, phosphorylation and the like. Such modifications are well known in the art. In another embodiment the invention provides a chimeric gene comprising the following operably linked DNA regions: a) a fiber cell preferential or fiber cell selective promoter selected from i) a nucleotide sequence comprising the nucleotide sequence of SEQ ID NO: 1 or SEQ ID NO: 2 or ii) a nucleotide sequence comprising the nucleotide sequence comprising at least 90%, particularly at least 95% sequence identity with SEQ ID NO: 1 or SEQ ID NO: 2 or iii) a nucleotide sequence comprising of an about 300 bp to an about 1300 bp DNA fragment hybridizing under stringent conditions with a nucleotide sequence mentioned under i) or ii), b) a heterologous DNA region encoding a biologically active RNA of interest and optionally c) a transcription termination and polyadenylation signal operable in plant cells. The term "heterologous" refers to the relationship between two or more nucleic acid or protein sequences that are derived from different sources. For example, a promoter is heterologous with respect to an operably linked DNA region, such as a coding sequence if such a combination is not normally found in nature. In addition, a particular sequence may be "heterologous" with respect to a cell or organism into which it is inserted (i.e. does not naturally occur in that particular cell or organism).

The term "chimeric gene" refers to any gene that contains: a) DNA sequences, including regulatory and coding sequences that are not found together in nature, or b) sequences encoding parts of proteins not naturally adjoined, or c) parts of promoters that are not naturally adjoined. Accordingly, a chimeric gene may comprise regulatory sequences and coding sequences that are derived from different sources, or comprise regulatory sequences, and coding sequences derived from the same source, but arranged in a manner different from that found in nature. In the current invention a "homologous" gene or polynucleotide or polypeptide refers to a gene or polynucleotide or polypeptide that shares sequence similarity with the gene or polynucleotide or polypeptide of interest.

"Fiber-selective" expression (or "transcription" or fiber cell selective which is equivalent) in the context of this invention means the transcription of a nucleic acid sequence by a promoter (or a transcription regulating element) in a way that transcription of said nucleic acid sequence in fibers contributes to more than 10 times, more than 20 times or even more than 100 times than the transcription of said nucleic acid sequence in most of the other plant tissues. In other words, in fiber-selective expression, transcription of the nucleic acid operably linked to the promoter of the invention in the fiber contributes to the degree of the transcription of said nucleic acid sequence described above in any single one tissue of most other plant tissues.

"Fiber-preferential" expression (or "transcription" which is equivalent) means the transcription of a nucleic acid sequence by a transcription regulating element in away that transcription of said nucleic acid sequence in fibers contributes to between 2 and 10 times of the transcription of said nucleic acid sequence in most of the other plant tissues. The term "fiber-enhanced" is equivalent to the term "fiber-preferential". In other words, in fiber-preferential expression, transcription of the nucleic acid operably linked to the promoter of the invention in the fiber contributes to between 2 and 10 times of the transcription of said nucleic acid sequence in any single one tissue of most other plant tissues.

The transcription sequences identified herein are found to mediate a strong expression preferentially or selectively in fiber, more specifically in the elongation stage and the secondary cell wall phase of the fiber. An expression cassette comprising SEQ ID NO: 1 and fragments thereof having promoter function direct the expression preferentially or selectively in fibers during fiber elongation and secondary cell wall formation of the fiber. An expression cassette comprising SEQ ID NO: 2 and fragments thereof direct the expression preferentially or selectively in fibers during fiber elongation and secondary cell wall formation of the fiber. More specifically, an expression cassette comprising SEQ ID NO: 1 or SEQ ID NO: 2 and fragments thereof direct the expression in the fibers preferentially or selectively between 10-35 days post anthesis (dpa).

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence. "Functionally linked" is an equivalent term.

As used herein, "promoter" means a region of DNA sequence that is essential for the initiation of transcription of DNA, resulting in the generation of an RNA molecule that is complementary to the transcribed DNA; this region may also be referred to as a "5' regulatory region." Promoters are usually located upstream of the coding sequence to be transcribed and have regions that act as binding sites for RNA polymerase II and other proteins such as transcription factors (trans-acting protein factors that regulate transcription) to initiate transcription of an operably linked gene. Promoters may themselves contain sub-elements (i.e. promoter motifs) such as cis-elements or enhancer domains that regulate the transcription of operably linked genes. The promoters of this invention may be altered to contain "enhancer DNA" to assist in elevating gene expression. As is known in the art, certain DNA elements can be used to enhance the transcription of DNA. These enhancers often are found 5' to the start of transcription in a promoter that functions in eukaryotic cells, but can often be inserted upstream (5') or downstream (3') to the coding sequence. In some instances, these 5' enhancer DNA elements are introns. Among the introns that are useful as enhancer DNA are the 5' introns from the rice actin 1 gene (see U.S. Pat. No. 5,641,876), the rice actin 2 gene, the maize alcohol dehydrogenase gene, the maize heat shock protein 70 gene (see U.S. Pat. No. 5,593,874), the maize shrunken 1 gene, the light sensitive 1 gene of *Solanum tuberosum*, the *Arabidopsis* histon 4 intron and the heat shock protein 70 gene of *Petunia hybrida* (see U.S. Pat. No. 5,659,122). Thus, as contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

Confirmation of promoter activity for a functional promoter fragment in fiber may be determined by those skilled in the art, for example using a promoter-reporter construct comprising the genomic sequence operably linked to a beta-glucuronidase (GUS) reporter gene as herein further explained. The fiber-preferential or fiber-selective expression capacity of the identified or generated fragments of the promoters of the invention can be conveniently tested by operably linking such DNA molecules to a nucleotide sequence encoding an easy scorable marker, e.g. a beta-glucuronidase gene, introducing such a chimeric gene into a plant and analyzing the expression pattern of the marker in fibers as compared with the expression pattern of the marker in other parts of the plant. Other candidates for a marker (or a reporter gene) are chloramphenicol acetyl transferase (CAT) and proteins with fluorescent properties, such as green fluorescent protein (GFP) from *Aequora victoria*. To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins, which are easily measured, including, but not limited to, chloramphenicol acetyl transferase (CAT), beta-glucuronidase (GUS), green fluorescent protein (GFP), beta-galactosidase (beta-GAL), and luciferase. The expression cassette containing the reporter gene under the control of the promoter can be introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography. The level of enzyme activity corresponds to the amount of enzyme that was made, which in turn reveals the level of expression and the fiber-specific functionality from the promoter or promoter fragment of interest. This level of expression can also be compared to other promoters to determine the relative strength of the promoter under study. Once activity and functionality is confirmed, additional mutational and/or deletion analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then again introduced in cells and their activity and/or functionality determined.

Instead of measuring the activity of a reporter enzyme, the transcriptional promoter activity (and functionality) can also be determined by measuring the level of RNA that is produced. This level of RNA, such as mRNA, can be measured either at a single time point or at multiple time points and as such the fold increase can be average fold increase or an extrapolated value derived from experimentally measured values. As it is a comparison of levels, any method that measures mRNA levels can be used. In a preferred aspect, the tissue or organs compared are a fiber or fiber tissue with a leaf or leaf tissue. In another preferred aspect, multiple tissues or organs are compared. A preferred multiple comparison is a fiber or fiber tissue compared with 2, 3, 4, or more tissues or organs selected from the group consisting of floral tissue, floral apex, pollen, leaf, embryo, shoot, leaf primordia, shoot apex, root, root tip, vascular tissue and cotyledon. As used herein, examples of plant organs are fiber, leaf, root, etc. and example of tissues are leaf primordia, shoot apex, vascular tissue, etc. The activity or strength of a promoter may be measured in terms of the amount of mRNA or protein accumulation it specifically produces, relative to the total amount of mRNA or protein. The promoter preferably expresses an operably linked nucleic acid sequence at a level greater than about 1%, about 2%, more preferably greater than about 5% of the total mRNA. Alternatively, the activity or strength of a promoter may be expressed relative to a well-characterized promoter (for which transcriptional activity was previously assessed).

It will herein further be clear that equivalent FS18 and SCW-PRP promoters can be isolated from other plants, preferably fiber producing plants. To this end, orthologous promoter fragments may be isolated from other plants using SEQ ID NO: 1 or SEQ ID NO: 2 or a functional fragment having at least 300 consecutive nucleotides thereof as a probe and identifying nucleotide sequences from these other plants which hybridize under the herein described hybridization conditions. By way of example, a promoter of the invention may be used to screen a genomic library of a crop or plant of interest to isolate corresponding promoter sequences according to techniques well known in the art. Thus, a promoter sequence of the invention may be used as a probe for hybridization with a genomic library under medium to high stringency conditions. As an alternative equivalent promoters can be isolated using the coding sequences of FS18 and/or SCW-PRP to screen a genomic library (e.g. by hybridization or in silico) of a crop of interest. When sufficient identity between the coding sequences is obtained (as a rule higher than 85% identity) then promoter regions can be isolated upstream of the orthologous FS18 and/or orthologous SCW-PRP genes.

Hybridization occurs when the two nucleic acid molecules anneal to one another under appropriate conditions. Nucleic acid hybridization is a technique well known to those of skill in the art of DNA manipulation. The hybridization property of a given pair of nucleic acids is an indication of their similarity or identity. Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence. "Stringent hybridization conditions" and "stringent hybridization wash conditions" in the context of nucleic acid hybridization experiments such as Southern and Northern hybridization are sequence dependent, and are different under different environmental parameters. An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M. Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code. Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3

M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., even more desirably still in 7% sodium dodecyl sulfate (SDS), 0.5 M NaPO$_4$, 1 mM EDTA at 50° C. with washing in 0.1×SSC, 0.1% SDS at 50° C.

In another embodiment of the present invention fiber-selective promoters are provided which comprise a nucleotide sequence having at least 40%, at least 50%, or at least 60%, or at least 70%, or at least 80%, or at least 90%, or at least 95% sequence identity to the herein described promoters and promoter regions and are also referred to as variants. The term "variant" with respect to the transcription regulating nucleotide sequences SEQ ID NO: 1 and 2 of the invention is intended to mean substantially similar sequences. Naturally occurring allelic variants such as these can be identified with the use of well-known molecular biology techniques, as, for example, with polymerase chain reaction (PCR) and hybridization techniques as herein outlined before. Variant nucleotide sequences also include synthetically derived nucleotide sequences, such as those generated, for example, by using site-directed mutagenesis of SEQ ID NO: 1 or 2. Generally, nucleotide sequence variants of the invention will have at least 40%, 50%, 60%, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence. Derivatives of the DNA molecules disclosed herein may include, but are not limited to, deletions of sequence, single or multiple point mutations, alterations at a particular restriction enzyme site, addition of functional elements, or other means of molecular modification which may enhance, or otherwise alter promoter expression. Techniques for obtaining such derivatives are well-known in the art (see, for example, J. F. Sambrook, D. W. Russell, and N. Irwin (2000) Molecular Cloning: A Laboratory Manual, 3$^{rd}$ edition Volumes 1, 2, and 3. Cold Spring Harbor Laboratory Press). For example, one of ordinary skill in the art may delimit the functional elements within the promoters disclosed herein and delete any non-essential elements. Functional elements may be modified or combined to increase the utility or expression of the sequences of the invention for any particular application. Those of skill in the art are familiar with the standard resource materials that describe specific conditions and procedures for the construction, manipulation, and isolation of macromolecules (e.g., DNA molecules, plasmids, etc.), as well as the generation of recombinant organisms and the screening and isolation of DNA molecules. As used herein, the term "percent sequence identity" refers to the percentage of identical nucleotides between two segments of a window of optimally aligned DNA. Optimal alignment of sequences for aligning a comparison window are well-known to those skilled in the art and may be conducted by tools such as the local homology algorithm of Smith and Waterman (Waterman, M. S. Introduction to Computational Biology: Maps, sequences and genomes. Chapman & Hall. London (1995), the homology alignment algorithm of Needleman and Wunsch (J. Mol. Biol., 48:443-453 (1970), the search for similarity method of Pearson and Lipman (Proc. Natl. Acad. Sci., 85:2444 (1988), and preferably by computerized implementations of these algorithms such as GAP, BESTFIT, FASTA, and TFASTA available as part of the GCG (Registered Trade Mark), Wisconsin Package (Registered Trade Mark from Accelrys Inc., San Diego, Calif.). An "identity fraction" for aligned segments of a test sequence and a reference sequence is the number of identical components that are shared by the two aligned sequences divided by the total number of components in the reference sequence segment, i.e., the entire reference sequence or a smaller defined part of the reference sequence. Percent sequence identity is represented as the identity fraction times 100. The comparison of one or more DNA sequences may be to a full-length DNA sequence or a portion thereof, or to a longer DNA sequence.

The promoters of the present invention may be operably linked to a nucleic acid sequence that is heterologous with respect to the promoter. The nucleic acid sequence may generally be any nucleic acid sequence for which an increased level or altered level (e.g. in a different organ) or reduced level of transcription is desired. The nucleic acid sequence can for example encode a protein of interest. Exemplary proteins of interest are e.g. polypeptides that can provide an agriculturally or industrially important feature in a fiber. Suitable heterologous nucleic acid sequences encoding a protein of interest include, without limitation, those encoding chitin synthases, nodulation protein C, sucrose synthase, expansins, callose synthases, fiber cell wall modifying proteins and the like.

In another embodiment the invention provides a vector, in particular a recombinant vector comprising an expression cassette of the invention. A "recombinant vector" refers to any agent such as a plasmid, cosmid, virus, autonomously replicating sequence, phage, or linear single-stranded, circular single-stranded, linear double-stranded, or circular double-stranded DNA or RNA nucleotide sequence. The recombinant vector may be derived from any source and is capable of genomic integration or autonomous replication.

Thus, any of the promoters and heterologous nucleic acid sequences described above may be provided in a recombinant vector. A recombinant vector typically comprises, in a 5' to 3' orientation: a promoter to direct the transcription of a nucleic acid sequence and a nucleic acid sequence. The recombinant vector may further comprise a 3' transcriptional terminator, a 3' polyadenylation signal, other untranslated nucleic acid sequences, transit and targeting nucleic acid sequences, selectable markers, enhancers, and operators, as desired. The wording "5' UTR" refers to the untranslated region of DNA upstream, or 5' of the coding region of a gene and "3' UTR" refers to the untranslated region of DNA downstream, or 3' of the coding region of a gene. Means for preparing recombinant vectors are well known in the art. Methods for making recombinant vectors particularly suited to plant transformation are described in U.S. Pat. No. 4,971,908, U.S. Pat. No. 4,940,835, U.S. Pat. No. 4,769,061 and U.S. Pat. No. 4,757,011. Typical vectors useful for expression of nucleic acids in higher plants are well known in the art and include vectors derived from the tumor-inducing (Ti) plasmid of *Agrobacterium tumefaciens*. One or more additional promoters may also be provided in the recombinant vector. These promoters may be operably linked, for example, without limitation, to any of the nucleic acid sequences described above. Alternatively, the promoters may be operably linked to other nucleic acid sequences, such as those encoding transit peptides, selectable marker proteins, or antisense sequences. These additional promoters may be selected on the basis of the cell type into which the vector will be inserted. Also, promoters which function in bacteria, yeast, and plants are all well taught in the art. The additional promoters may also be selected on the basis of their regulatory features. Examples of such features include enhancement of transcriptional activity, inducibility, tissue specificity, and developmental stage-specificity.

The recombinant vector may also contain one or more additional nucleic acid sequences. These additional nucleic acid sequences may generally be any sequences suitable for use in a recombinant vector. Such nucleic acid sequences include, without limitation, any of the nucleic acid sequences, and modified forms thereof, described above. The additional structural nucleic acid sequences may also be operably linked to any of the above described promoters. The one or more structural nucleic acid sequences may each be operably linked to separate promoters. Alternatively, the structural nucleic acid sequences may be operably linked to a single promoter (i.e., a single operon).

The present invention is also directed to transgenic plants and transformed host cells such as plant cells which comprise a promoter operably linked to a heterologous nucleic acid sequence as described herein. Other nucleic acid sequences may also be introduced into the plant or host cell along with the promoter and structural nucleic acid sequence, e.g. also in connection with the vector of the invention. These other sequences may include 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

The term "transformation" herein refers to the introduction (or transfer) of nucleic acid into a recipient host such as a plant or any plant parts or tissues including plant cells, protoplasts, calli, roots, tubers, seeds, stems, leaves, seedlings, embryos and pollen. Plants containing the transformed nucleic acid sequence are referred to as "transgenic plants". Transformed, transgenic and recombinant refer to a host organism such as a plant into which a heterologous nucleic acid molecule (e.g. an expression cassette or a recombinant vector) has been introduced. The nucleic acid can be stably integrated into the genome of the plant.

As used herein, the phrase "transgenic plant" refers to a plant having an introduced nucleic acid stably introduced into a genome of the plant, for example, the nuclear or plastid genomes.

In some embodiments of the present invention, one or more components of a plant, cell, or organism are compared to a plant, cell, or organism having a "similar genetic background." In a preferred aspect, a "similar genetic background" is a background where the organisms being compared share about 50% or greater of their nuclear genetic material. In a more preferred aspect a similar genetic background is a background where the organisms being compared share about 75% or greater, even more preferably about 90% or greater of their nuclear genetic material. In another even more preferable aspect, a similar genetic background is a background where the organisms being compared are plants, and the plants are isogenic except for any genetic material originally introduced using plant transformation techniques.

A transformed host cell may generally be any cell that is compatible with the present invention. A transformed host plant or cell can be or derived from a monocotyledonous plant or a dicotyledonous plant.

Accordingly, the present invention is directed to transgenic plant cells and transgenic plants which comprise the promoter of the invention or the chimeric gene of the invention as described above, i.e. the promoter sequence disclosed herein, operably linked to a heterologous nucleic acid sequence encoding biologically active RNA; or which comprise the plant cell of the invention. Preferred promoter sequences and expression products of interest and other regulatory elements, are described above.

A transgenic plant may be produced by introducing the nucleic acid sequence(s) as described above into plants or plant cells. "Introducing" in connection with the present application relates to the placing of genetic information in a plant cell or plant by artificial means. This can be effected by any method known in the art for introducing RNA or DNA into plant cells, protoplasts, calli, roots, tubers, seeds, stems, leaves, seedlings, embryos, pollen and microspores, other plant tissues, or whole plants. More particularly, "introducing" means stably integrating into the plant's genome.

Plants containing transformed nucleic acid sequence are referred to as "transgenic plants". Transgenic and recombinant refer to a host organism such as a plant into which a heterologous nucleic acid molecule (e.g. the promoter, the chimeric gene or the vector as described herein) has been introduced. The nucleic acid can be stably integrated into the genome of the plant.

A number of methods are available to introduce DNA into plant cells or plants by transformation. *Agrobacterium*-mediated transformation of cotton has been described e.g. in U.S. Pat. No. 5,004,863, in U.S. Pat. No. 6,483,013 and WO2000/71733.

Plants may also be transformed by particle bombardment: Particles of gold or tungsten are coated with DNA and then shot into young plant cells or plant embryos. This method also allows transformation of plant plastids. Cotton transformation by particle bombardment is reported e.g. in WO 92/15675.

Viral transformation (transduction) may be used for transient or stable expression of a gene, depending on the nature of the virus genome. The desired genetic material is packaged into a suitable plant virus and the modified virus is allowed to infect the plant. The progeny of the infected plants is virus free and also free of the inserted gene. Suitable methods for viral transformation are described or further detailed e.g. in WO 90/12107, WO 03/052108 or WO 2005/098004.

Further transformation protocols can also be found in U.S. Pat. No. 7,172,881.

The plant cell may be derived from any trichome-producing plant, such as *Gossypium* (cotton), *Nicotiana*, *Arabidopsis* as well as the fiber producing plants described above. In one example, the plant cell is derived from *Gossypium*.

"Cotton" or "cotton plant" as used herein can be any variety useful for growing cotton. The most commonly used cotton varieties are *Gossypium barbadense*, *G. hirsutum*, *G. arboreum* and *G. herbaceum*. Further varieties include *G. africanum* and *G. raimondii*. Also included are progeny from crosses of any of the above species with other species or crosses between such species.

A cotton plant cell may be any cell comprising essentially the genetic information necessary to define a cotton plant, which may, apart from the chimeric gene disclosed herein, be supplemented by one or more further transgenes. Cells may be derived from the various organs and/or tissues forming a cotton plant, including but not limited to fruits, seeds, embryos, reproductive tissue, meristematic regions, callus tissue, leaves, roots, shoots, flowers, vascular tissue, gametophytes, sporophytes, pollen, and microspores. Whereas certain plant cells according to the invention may be able to regenerate into complete plants, in some embodiments, said plant cells cannot further develop or regenerate into a complete plant.

The present application also discloses a transgenic plant consisting of the transgenic plant cell described hereinabove, or comprising the chimeric gene or the vector described herein stably integrated in the plant genome. This may be effected by transformation protocols described elsewhere in this application.

In another embodiment, the present invention relates to a seed generated from a transgenic plant described herein, wherein said seed comprises the chimeric gene described herein.

Seed is formed by an embryonic plant enclosed together with stored nutrients by a seed coat. It is the product of the ripened ovule of gymnosperm and angiosperm plants, to the latter of which cotton belongs, which occurs after fertilization and to a certain extent growth within the mother plant.

Further disclosed herein are cotton fibers and cotton seed oil obtainable or obtained from the plants disclosed herein. Cotton fibers disclosed herein can be distinguished from other fibers by applying the detection method disclosed in WO2010/015423 and checking for the presence of the promoter or chimeric gene of the invention in the fibers. Accordingly, the promoter may also be used for tracking cell walls, in particular cotton fibers according to the invention.

Also disclosed herein are yarn and textiles made from the fibers disclosed herein as well as foodstuff and feed comprising or made of the cotton seed oil disclosed herein. A method to obtain cotton seed oil comprising harvesting cotton seeds from the cotton plant disclosed herein and extracting said oil from said seeds is also disclosed. Further, a method to produce cotton fibers comprising growing the cotton plant disclosed herein and harvesting cotton from said cotton plants is also disclosed.

In another embodiment, the present invention discloses a method of producing a transformed plant cell or plant, comprising introducing the chimeric gene of the invention into a parental plant cell to produce a transformed plant cell, and optionally regenerating a plant from said transformed plant cell.

The invention furthermore relates to the use of a chimeric gene of the invention to produce a transformed plant cell.

A method of producing altered fiber, comprising (i) growing the plant of the invention, and (ii) harvesting the fiber from the plant.

Altered fiber harvested from a plant of the invention or produced by the method of the present invention.

In another aspect, the present application discloses to a method of producing a seed comprising the chimeric gene disclosed herein comprising (a) growing a transgenic plant comprising the chimeric gene described herein or the vector described herein, a transgenic plant described herein or a transgenic plant obtained by the method described herein, wherein said transgenic plant produces said seed and said chimeric gene is comprised in said seed, and (b) isolating said seed from said transgenic plant.

In one example of the method of producing a transgenic plant or the method of producing a seed, the plant is a cotton plant as described elsewhere in this application.

In another aspect, the present application discloses to a method of effecting fiber-preferential or fiber-selective expression of a product in cotton comprising introducing the chimeric gene disclosed herein or the vector disclosed herein into the genome of a cotton plant; or providing the transgenic plant disclosed herein.

In a further aspect, the present application discloses a method of altering fiber properties in a cotton plant comprising introducing the chimeric gene disclosed herein or the vector disclosed herein into the genome of a cotton plant; or providing the transgenic plant disclosed herein.

In one example, the method further comprises growing said plant until seed are generated.

In another example based on the above further step, the method is for increasing cotton yield from a cotton plant and further comprises harvesting the cotton produced by said cotton plant. In other words disclosed herein is a method for increasing cotton yield from a cotton plant comprising introducing the chimeric gene disclosed herein or the vector disclosed herein into the genome of a cotton plant; or providing the transgenic plant disclosed herein; growing said plant until seed are generated; and harvesting the cotton produced by said cotton plant.

The term "increasing the yield" in connection with the present application relates to an increase in the output of cotton fibers which can be achieved e.g. by increasing the number of fibers produced on a cotton seed, the length of the fibers or the strength of the fibers. Genes and expression products thereof involved in conferring these properties have been described above.

In another aspect, the present application discloses the use of the chimeric gene disclosed herein, the vector disclosed herein or the transgenic plant or plant cell disclosed herein for fiber-preferential or fiber-selective expression of a product in cotton, for altering fiber properties in cotton or for increasing cotton yield. The definitions and further examples described above for other aspects disclosed herein equally apply to the present aspect.

The following non-limiting Examples describe the methods for isolating the fiber selective promoters. Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK.

Throughout the description and examples, reference is made to the following sequences represented in the sequence listing:

SEQ ID NO: 1: promoter sequence derived from the cotton FS18 gene

SEQ ID NO: 2: promoter sequence derived from the cotton SCW-PRP gene

SEQ ID NO: 3-SEQ ID NO: 18: artificial sequences and primers

SEQ ID NO: 19: nucleic acid sequence encoding the *Neurospora crassa* chitin synthase 2 gene (Din and Yarden, 1994)

SEQ ID NO: 20: Golgi-targeting signal from *Arabidopsis thaliana* (Pagny et al., 2003)

SEQ ID NO: 21: coding sequence of the double mutant of the 5-enol-pyruvylshikimate-3-phosphate synthase (epsps) gene of *Zea mays* (Lebrun et al., 1997)

SEQ ID NO: 22: coding sequence of the bar gene (phosphinotricin acetyltransferase gene) of *Streptomyces hygroscopicus* (Thompson et al., 1987)

SEQ ID NO: 23: coding sequence of the gfa (glutamine: fructose-6-phosphate amidotransferase) gene from *E. coli* (Frohberg and Essigmann, 2006)

SEQ ID NO: 24: primer Q-GUS

SEQ ID NO: 25: primer Q-ME

SEQ ID NO: 26: primer FS18 Up

EXAMPLES

Example 1

1. Introduction and General Strategy for the Identification of Fiber Selective Promoters In our research we aimed at the isolation of specific cotton promoters for their ability to drive the expression of chimeric genes selectively in fibers, preferably with an activity starting at the fiber elongation stage and continuing until the fiber secondary cell wall synthesis. In our experimental strategy we used both genomic tools and a candidate gene approach to isolate and test a number of cotton promoters. Bioinformatic analysis of published and existing gene expression data (EST collections, differential display, microarray analysis and candidate gene analysis) were used to identify potential candidate genes that are expressed predominantly or exclusively in cotton fibers. In our initial analysis a first list of about 450 potential fiber expressed genes was generated. This list was narrowed down through a process of examining the frequency of occurrence of ESTs homologous to those genes in public databases (as a surrogate of transcript abundance). Subsequently quantitative RT-PCR and/or Northern blotting on a range of tissue types was used to validate the expression profiles deduced from the literature or other data, initially just comparing expression levels at two different fiber stages to the expression levels in leaves, stems and roots of the same plants using available RNAs or tissues. The comparison with expression levels in non-fiber tissues was used to establish that the promoters were fiber selectively or preferentially expressed in fibers. Next, the promoter regions of the candidates were isolated either through BAC library screening (BAC filters available from Clemson Genomics Institute of *G. hirsutum* cv. Acala Maxxa), or if the full length cDNA or tentative consensus cDNA sequence was available by inverse PCR or Genome Walker Amplification kits. The resulting promoter sequences were linked to a reporter gene (e.g. GUS) and, in a first step, evaluated by particle bombardment of cotton ovule tissues to verify that the construct was functional. In a second step, transgenic cotton plants were generated via *Agrobacterium* transformation to introduce the chimeric genes comprising the promoter-reporter gene constructs into cotton. Finally, expression profiles in the transformed plants were analyzed by quantitative and histochemical GUS staining to confirm the promoter's fiber specificity and expression.

2. Isolation of the FS18 Promoter

FS18 was a fiber expressed gene originally identified by Orford and Timmis (1997) *Theor Appl Genet.* 94: 909-918, by differential screening of fiber cDNAs from *G. hirsutum*. The initial cDNA clone was only 97 bp in length and formed part of a transcript estimated to be about 700 bases in length. This was then used as a probe in library screening to obtain two longer polyadenylated cDNA clones of 616 bp and 610 bp, respectively, called FS18 and FS18A (Orford et al. (1999) *Theor Appl Genet* 98: 757-764. The proteins encoded by the genes corresponding to FS18 and FS18A were probably non-specific lipid transfer proteins, many of which were expressed in fibers.

By using the FS18 or FS18A nucleotide sequences in a Megablast search with default parameters and a cut-off E value of E-100 of the most recent Genbank *Gossypium* species EST database (Release No: 177), including all known diploid and tetraploid *Gossypium* ESTs, it was apparent that these FS18-like genes were likely to be relatively fiber specific and expressed in elongating and early SCW thickening stage fibers. This analysis, however, did not distinguish between the two putative homologous genes in tetraploid cotton. Using a more specific approach by searching (BLASTn) only the *G. hirsutum* ESTs in Genbank with a gene specific region of approximately 150 bp from the middle of the cDNA where the highest sequence variation between the two genes occurred (75% identity in this region), a better picture of the expression patterns of these two genes at a gross tissue level was obtained. Megablast only detected 10 ESTs with high similarity to FS18A (E value less than E-50) while it detected 294 ESTs for FS18, so the latter gene was clearly the more highly expressed gene in cotton fibers and a more suitable target for promoter isolation. Both genes appeared to be fiber-selective and to be equally represented in both elongating fiber (0-10 dpa) and early SCW stage fiber cDNA libraries around 20-22 dpa.

Sequences used for gene-specific Megablast searches:

```
1) FS18
                                                          (SEQ ID NO: 3)
1 GATGGCTTAG TCGGCCTCCC ACGCTGCCTT CCTTTTTTGT CAGGGAATGG    50

TGATGGTGCT GATGCCACAG GTTGCTGTGC CATCGTCATG AATGCCTTGG   100

GATCGCTCTG TGGTGATACA TAGGAACCGA TCTAGCT                 137

2) FS18A
                                                          (SEQ ID NO: 4)
1 GATGGCGTAG TCACCCTTCC ACGCTGCCTT CCTTTATTGA TAGGGAATGG    50

TAATGGTGCT GATGCTGATG TTGATGCCCC AGCTTGCTGC GACATCGTCA   100

GGGGTCTCTT GAGCTCGCTGC TCTGTGGTGG TGTTTAGGAA CCGATCTAGCT 151
```

Primers were designed to the 3'UTR of FS18 for Q-PCR and used to profile the relative expression of FS18 and FS18A in different tissues of plants of the *G. hirsutum* cultivar Coker 315, using the ubiquitin gene as a reference for the expression levels. RNA preparation was carried out according to Wan and Wilkins (1994) (Anal Biochem 223: 72-12) with up to 2 g ground fibers or other tissues. All RNA preparations were DNAse treated and purified by organic extraction. In Real-Time PCR experiments, we used 5 µg of total RNA for the production of cDNA according to the manufacturer's recommendations (Superscript II, BRL Life Technologies, Gaithersburg, Md., USA) with cDNA priming from oligo-dT (0.5 µg of dT18). The primers used were Primer 3 (frodo.wi.mit.edu/cgi-bin/primer3/primer3_www.cgi) and FS18_F: 5'-ctagcttgaaatcgggttcg-3' (SEQ ID NO: 5) and FS18_R: 5'-ttggatcccacccttaaaca-3' (SEQ ID NO: 6) and were designed to amplify a product of 89 bp. The second primer for FS18 had a single mismatch with FS18A, but was thought likely to detect both transcripts. The primers for the cotton RNA Helicase gene used as a reference in the PCR reactions were RNAHel_F:

1 agcctgatcg_atatgtggag_ggat 24

(SEQ ID NO: 7) and RNAHel_R:

1 tcaggaaggt_ttggccatct_tgga 24

(SEQ ID NO: 8); they amplified a product of 180 bp (Hovav et al, 2007: Planta 227, 319-329). Real time PCR experiments were carried out using an Applied Biosystems 7900HT Fast Real-time PCR system (CA.USA) according to the following procedure. 15 µL of a master mix consisting of 10 µl of 2×SYBR Green JumpStart Taq Ready Mix (Sigma), 0.5 µL of each 20 µM forward and reverse oligonucleotides corresponding to the given target gene and 4 µL of PCR grade water were pipetted into 96 well plates. The templates (5 µL of a 1/500 dilution of the cDNA reaction) were then added to the master mixes and transferred to the thermal cycler. Cycling conditions were 5 min of denaturation at 95° C. followed by 40 cycles of 95° C. denaturation for 15 seconds, 60° C. annealing for 15 seconds and 72° C. elongation for 20 seconds. Following amplification, a dissociation stage was carried out to detect any complex products. Data analysis was performed with RQmanager V1.2 software (Applied Biosystems) and relative transcript abundance compared to 0 dpa ovules determined using the cotton helicase gene as an internal standard using the ΔΔCt method.

According to the q-PCR data (see FIG. 1), FS18 was highly expressed in fibers (from 10 through to 35 dpa), although highest in about 20 dpa fibers, with a small amount of expression in some other floral tissues like stigma.

In a next step, we isolated the FS18 promoter. Thereto a fragment of the 5' end of the FS18 cDNA was used as a probe to screen a large insert BAC library from G. hirsutum cv Acala Maxxa (GH_MBb, Clemson Genomics Institute) according to the suppliers recommended protocol (www.genome.clemson.edu/resources/protocols) and the three strongest hybridising BACs were selected for sequencing (BAC3P22, 241H24 and 213B4).

Sequencing upstream from a primer in the 3'UTR of FS18 (FS18Up, SEQ ID NO: 26:

1 tgtatcacac_aattggatcc_cacc 24)

through the coding region indicated that these three BACs were very similar to each other and FS18. Specifically, 3P22 was identical to FS18 in the coding region and 241H24 and 213B4 were identical to each other but had a single non-conservative base substitution relative to FS18.

It was clear that all these BACs encoded an FS18 gene rather than an FS18A type as they lacked the insertions and base substitutions seen in FS18A, and it was concluded they might represent two very closely related FS18 gene family members. Neither gene contained an intron. A primer walking strategy was then used to sequence upstream from the coding region into the promoter of the genes on BAC3P22 and BAC241H24. The promoter sequences of both genes were extremely similar (99% identical) so it was likely they were the result of a relatively recent duplication of an ancestral gene. Only the gene encoded by 3P22 was studied further.

```
                                                              SEQ ID NO: 1
        1    aatggatcgg gcctcgagta agaatttttt ggtccgagcc caacccagat   50 ttacaaaaaa attgttgttg ttgttttttct actgttttat tgtcatttca  100 ctattatatt gttattgttt tgttgttatt atcacacggc cgtgtgtcac  150 acataggcat gtgccttgag cgtgttgaaa aatagtatag gtgtagtttc  200 cacacggtct gacacacggt cgtgtatctc aagtcaatga gttacacaga  250 tagagacacg ggctgggata cggccatgtg tcccaacttt gaaagtcaca  300 cggcctgggg cattccacac gatcgtgtgt ctcctgtttc taggcacttt  350 gagatttcac cctaaacttc tagaattgtt tcaaattagc ccctatttgt  400 tcttaaatca ttttagggcc ctgtaaactc atatttagga ctaaatgggt  450 aatttttact atgatttgaa tgaattagct tgcattttaa ttatgattga  500 tttgataata atgcccgtga ccctaatccg ttggcggaga ggggttaggg  550 gttttattgt tattttttag atattgtata gctcttgttt ttttgttaat  600 tttgttatta ttttaaaggc atttgtttgt taagttacac ctatcttaat  650 gttatttctg gtaggtttta tgggtgaata acccttgacc accaaatcaa  700 tcacaagagt tcaatatttt atttatttta aaatgtattg aaaatcgtta  750 atctatatat ttgcctatta ttggattaaa tattcataag agtttagacc  800 gtcgtgagac aagttagttt tatctaactg atggtcatcg cacttagtta  850 aaaagttagt ggcgcaaagc taccatgcgg tggattatga ttgaatgtct  900 ctaaatcaga atcaggatta gaaacgacgc acacttctgt tgcccgattg  950
```

```
ccgaccccaa tgacacgtgt tgtaggttta gccatcttta tgaaagataa 1000
tgttttctgt tttataagta agcaactata ggggtttact tcggtacgca 1050
aatttttagg ttaactattt tgggaagggc cattatgatt caattgaaag 1100
aaagttggca cacacaaaat cactacatct gttttgacag agacacagcc 1150
taaaaacagc agcaaacaag cctaaaggaa tcacccaaaa acaacaacca 1200
aaagtacaga ggaaaacaaa agaatccctg ctaccaccaa gctgaaaaaa 1250
agaaaataaa aactcaactt ttggctataa aaaccctcct accctcaacc 1300
cctaaccacg caacaatcag caatactcca agcaaccatt ttccttacaa 1350
gtttgttttt cttgtgatta atccat                          1376
```

A 1376 bp fragment of the promoter (SEQ ID NO: 1) upstream from the ATG codon was amplified from BAC DNA of 3P22 using the gateway primers gwFS18Pro_F 1 ggggacaagt_ttgtacaaaa_aagcaggcta_atggatcggg_cctcgagta 49

(SEQ ID NO: 9) and gwFS18Pro_R 1 ggggaccact_ttgtacaaga_aagctgggta_tggattaatc_ acaa-gaaaaa_ca 52

(SEQ ID NO: 10) (gene-specific sequences are in bold) containing the attB1 and attB2 recombination sites for in vitro recombination using the Gateway cloning system (Invitrogen). PCR amplification form BAC DNA followed by PEG cleanup according to the manufacturer's instructions and in vitro recombination using the BP reaction with the intermediate vector pDONR201 (Invitrogen) and transformation into DH5a cells resulted in the production of pDONR/FS18pro (3P22). The intermediate vector was sequenced with pDONR-F and pDONR-R primers (Invitrogen) and then recombined into a GUS reporter gene destination vector pSirogateIV-GUS using the LR reaction as recommended. The pSirogateIV-GUS vector contained the left and right borders of the T-DNA, a promoterless GUS gene downstream from an attR gateway recombination cassette, a transcription terminator/polyadenylation sequence from a *Flavaria bidentis* malic enzyme and a plant expressible kanamycin resistance gene with a promoter from the segment 1 sub-genomic RNA and terminator of segment 3 of the sub-clover stunt virus as described in Schunmann et al. (2003) *Funct Plant Biol* 30: 443-452.

The resulting plasmid pSirogateIV-FS18-GUS was sequenced with a primer in the GUS reporter gene (GUSRev:

1 tccagactga_atgcccacag_g 21

SEQ ID NO: 18) to confirm the correct recombination of the promoter and then transferred to *Agrobacterium* strain AGL1 (Lazo et al (1991) *Biotechnol.* 9: 963-967) by electroporation.

In a first step the functionality of the promoter was tested in a transient expression assay by particle bombardment of pSirogateIV-FS18(3P22)-GUS DNA into cultured cotton ovules and staining for GUS enzyme activity according to Jefferson et al (1987) *EMBO J.* 6: 3901-3907.

In this experiment an expression vector comprising a 35S promoter-GUS cassette was used as a control. The activity of the promoter was monitored by counting the number of GUS spots/number of ovules analyzed (see Table 1).

TABLE 1 number of GUS spots/number of ovules analyzed. The FS18 promoter was able to drive GUS expression between 16 dpa and 29 dpa.

| promoter | 7 dpa | 16 dpa | 29 dpa |
|---|---|---|---|
| 35S | 10/40 | 1/10 | not tested |
| FS18 | not tested | 2/30 | 5/28 |

In a next step, cotton transformation with the *Agrobacterium* strain carrying pSirogateIV-FS18-GUS was carried out essentially as described in Murray et al. (1999) *Mol. Breed.* 5: 219-232 using seedling cotyledon segments of cotton cultivar Coker315-11 (a CSIRO selection from the regenerable Coker 315 cultivar) and selection for resistance to kanamycin sulphate.

A total of 19 primary transformants were generated representing 14 independent transformation events. Plants were transferred to soil and allowed to flower. Flowers were tagged at anthesis and both 10 and 20 dpa bolls collected and whole developing seeds with fibers stained for GUS enzyme using X-gluc histochemical stains as described by Jefferson et al. (1987) *EMBO J.* 6: 3901-3907.

Figure 2:
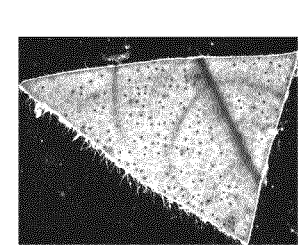
FIG. 2: GUS staining patterns for a representative transformant containing the FS18 promoter-GUS construct. Note blue staining in 10 and 20 dpa fibers and a small amount of staining in an epidermal gland distributed across the surface of young leaf petioles. No staining was observed in vegetative trichomes.
Figure 2:
Figure 2:
Figure 2:
Figure 2:
Figure 2:
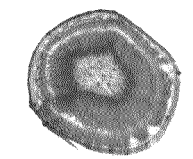

Immature leaves, petiole segments, roots and stem sections from both young and older branches were also stained for GUS. Observed staining patterns are summarized in Table 2 and representative images are shown in FIG. 2.

TABLE 2

| Transformant line | Leaf | Petiole | Stem | Root | 10 dpa fiber | 20 dpa fiber |
|---|---|---|---|---|---|---|
| T420-48 | − | + Some weak staining in a few surface glands, no staining in trichomes | − | − | +++ | +++ |
| T420-2 | − | − | − | − | +++ | +++ |
| T420-37 | − | + Some weak staining in a few surface glands, no | + Some weak staining in a few surface glands, no | − | +++ | +++ |

TABLE 2-continued

| Transformant line | Leaf | Petiole | Stem | Root | 10 dpa fiber | 20 dpa fiber |
|---|---|---|---|---|---|---|
| | | staining in trichomes | staining in trichomes | | | |

Tissues in which GUS enzyme activity were detected in different T₀ transgenic cotton plants transformed with the SirogateIV-F518 promoter-GUS construct. +, weak or localized expression, ++ medium expression, +++ very strong expression, – no staining.

It can be seen in FIG. 2 that the FS18 promoter is highly fiber selective although there is a small amount of expression in a small glandular trichome on petioles and stems.

3. Isolation of the SCW-PRP Promoter

Ji et al (2003) *Nucleic Acids Res.* 31: 2534-43, identified a short 230 bp cDNA clone P2G01 (CB350474) by subtractive PCR using cDNA obtained from 10 dpa fibers and cDNA from a fiberless mutant as a driver followed by differential screening on a nylon macroarray against fiber cDNAs of different ages. The clone was one of about 30 differentially expressed fiber genes. Expression of the gene appeared to turn on at about 5 days post anthesis (dpa) and continued to be expressed up to the 20 dpa stage tested. The protein encoded by P2G01 was designated in Ji et al (2003) as a vacuolar (H+)-ATPase catalytic subunit but our analysis suggested it was more likely to be a proline rich protein. P2G01 (CB350474) was not expressed at 0 dpa but increased in expression to moderate levels in 5, 10 and 20 dpa fibers. Matches to CB350474 were identified from a Megablast search of Genbank *G. hirsutum* cotton fiber ESTs and a 659 bp consensus transcript (SEQ ID NO: 11) sequence derived from a number of overlapping ESTs was obtained.

did not reveal convincing matches with other proteins except to a small region in another putative cotton PRP (ABM05951), PRP3.

The consensus transcript sequence was used to query cotton EST libraries using MegaBlast. Hits with an E value of <–100 were counted and then grouped according to the tissue source of the cDNA library from which they were derived. Transcripts closely matching to CB350474 were slightly less abundant than those for FS18, but were only found in fiber cDNA libraries, with about twice as many from early SCW stage fibers of 20-22 dpa than in elongating fibers of 0-10 dpa. The gene was therefore designated a SCW PRP.

Primers spanning the 3' end of the consensus transcript were designed for q-PCR to measure the expression level of the gene corresponding to the cDNA for SCW PRP. They were SCWPRP_F 1 caggtacacc aatcgaggaa 20

(SEQ ID NO: 12) and SCWPRP_R 1 atggtgggat tgttggtagc 20

Figure 3:
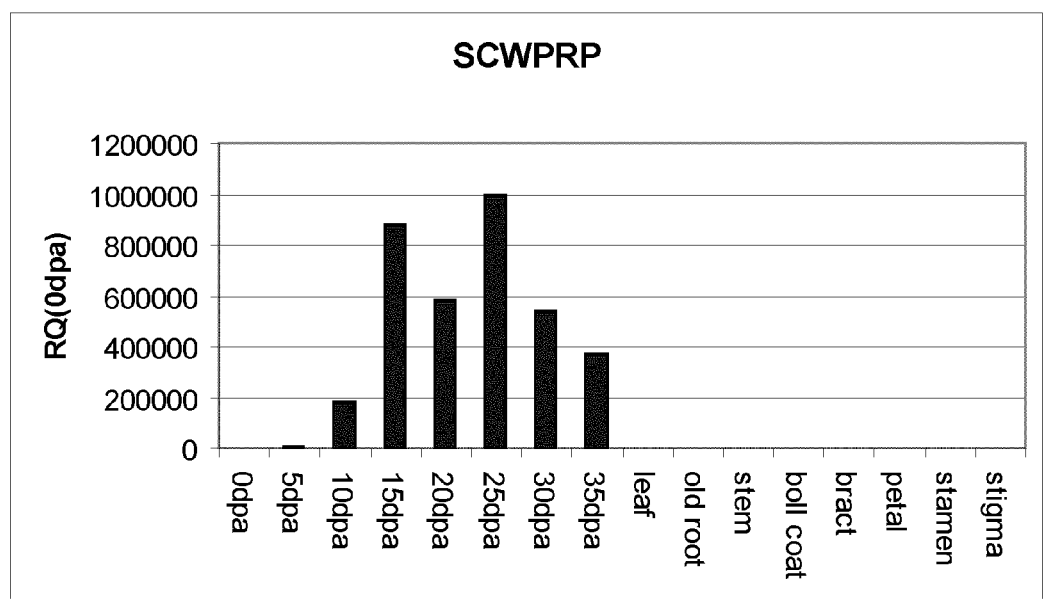
FIG. 3: The proline rich cell wall protein, SCWPRP, is expressed throughout fiber development in both the elongation and cell wall thickening stages and was not detected in any other tissues tested. Relative expression by quantitative RT-PCR of the SCW PRP in different tissues using the cotton RNA helicase gene as a reference. Values are the average of four technical replicates.

(SEQ ID NO: 13) which produced a product of 110 bp in the amplifications. As for the measurement of expression levels of the FS18 gene, the cotton RNA Helicase was used as a reference gene in the quantitative PCR assays and the expression level at different time points after anthesis relative to 0 dpa determined. It can be observed in FIG. 3 that the expression of the SCWPRP gene was fiber-selective.

A 330 bp fragment spanning the coding region of the SCW PRP gene was amplified from 20 dpa cotton fiber cDNA and used as a probe to screen the Acala Maxxa large insert BAC filters (Clemson Genomics Institute) as described above. 13 Different BACs were isolated and sequenced using a primer from near the translation start (SCWPRP-down

```
                                                       (SEQ ID NO: 11)
5'
1 cgcggggaac tcaaatcttc aatctttaga tcatctctcc aaaaaaatat ggcaggttcc   60 aacgttttca ttttaatagc ttgcttcatt ttgttgggtt tttcaagtat ggaggttagc  120 ctagcaactc gaaatattca gcacgtgtca ctaattgaag tgtcaccaat aacattgtcg  180 ttattcccac cattgccacc aataagatct ccgttcttgc caccaatacc accaataaca  240 ttgtcaccaa tgacattggc accaataaca ttgacaccaa caggtacacc aatcgaggaa  300 ccaatagatc caccaaccga gaaaccaaca gatccaccaa ctgaggtacc aacactgcct  360 tgaatcccaa agctaccaac aatcccacca tcttagccta agcctatcac tgttcttcca  420 caagttccca gcaatagctt gccttccatt cctttcatgt ctccatctcc acctccacct  480 ccacctccat ccagctattg aagacaattt gattcctaat tagtatcaca tatattactg  540 agaatgaact ctgtcatcac attctctatg atgttatttc atgaaataag aatgtagttt  600 ctatttacat tttacatata taataaagtg tggtgttttt tttaaaaaaa aaaaaaaa    659
```

The consensus transcript encoded a small 104 amino acid protein with a predicted signal peptide at the NH₂ terminus (prediction using SignalP, Emanuelsson et al., 2007 *Nature Protocols* 2, 953-971). The existence of the signal peptide predicted secretion of the mature protein out of the cell into the cell wall. It contained no protein domains conserved in sequence, but the predicted mature protein of 78 AA contained 28.4% proline. We have therefore called it a proline-rich protein (PRP), although searching of protein sequences using BlastP or of the nucleotide sequences using BLASTx 1 gcaggttcca acgttttcat 20
SEQ ID NO: 14)
This identified two classes of genes that were very similar and represented by BAC clones BAC4A23 and BAC1001. The SCW PRP genes on these BACs were sequenced more fully. Neither gene had an intron. The gene in BAC4A23 matched the consensus cDNA sequence exactly while that in BAC10G1 had three nucleotide differences to the consensus SCW PRP transcript so they represented very similar genes. The nucleotide sequence present in BAC4A23 (SEQ ID NO: 15) was analyzed in detail.

SEQ ID NO: 15

```
1   aactagtgaa acagatacaa acttgtgtta gattctacag aagtaaaaat aaattatttg   60
    gggtgttaca ttgttaatat tttaaacata atcataagtt taaggaccta tctaaaatta  120
    gaccaataaa atttaaaata taaatatgat attgtttctt ggatttatag aataatggat  180
    tgttatatac atagtatgag atgatctatt gattctatat tcttaccgtt gaatttatga  240
    atttttttc ttatttcttt tgagtttgat taatgatgta ctgtatttat atgtttatcg  300
    aagaatattt tatatttaaa atttattaa tctcattagt tgatacttgt cttttttgtt  360
    cttcacggaa agttgttata tataagttca gtaaataata atgaaatata aattttaatt  420
    atatctagta ctcaataaga agatggagaa agttatgtta attatagtta taaattattt  480
    ataaatttaa tatatatata taaagaaaat agttgtataa ctaataatta tttttacaat  540
    actttatata gttatattta aaaaaatttt aaaattaaaa tactattatt ttgttcaata  600
    tattaatatt tatattattt aatttattat tgaatatgaa taaattttt ttgaaaatta  660
    tattttaat ttttagaaat tttatataac tttccatata tatatttctg atttgtcaat  720
    ttcttttgag atttatctaa attgatttga atttttttta tttttaaaaa ataaaataat  780
    tttaaaattt cttggaattt tatataaatt tttggatttt tcaaaaaaa ttgagatttt  840
    tttcttttt ttcgatttt taaatttatt tcaggaaaat ataaactaac ttttctttgc  900
    tttgggtata attaatatta gataacccac aaattagatc aataggagct tcatgtccta  960
    atcccattta attacttttg ttgtatcatt aatttagtcg accttacata gtagctctat 1020
    ggggcaaata gttataaatg ttaaattagt atttaaatct tgaagttttt aatttaaagt 1080
    tcagactatt agtattatat caaatattta agggtaaata tatattctaa tatctaagct 1140
    tgggtcaagg tttaaattaa gtacttaaac ttggttttat agttcaaatt gatttaaata 1200
    actaagtatt aatttgaatt aagaagcaaa gttcaagtac ctaattagac tataaaaaaa 1260
    acttttgcta gtaaattgaa ccttaaagtc gagtttagtt atctaattgg acaaaaaaat 1320
    cttaaatacc aatttaaacc ctaaagtcaa gtttaggtac caaagtgtat atttatctaa 1380
    tatttaaatt tgatccacct aattaaaatt ttttggtcc aatgcaataa gagaattaat 1440
    taatacttac acacatgata gagatatacc cacaacagat acacactaca aaaaacatta 1500
    aaaaatagaa agatatatt cctacaaaat ttaaaagcat ttaatttttt aactaacatt 1560
    agacaaatgg aaatggaaag acttattttt aagtttatgg atgaatctaa tttatctaaa 1620
    cattgggttt tttttttttg tgacgaaata tgggtgagag aaggtagtaa gctaagtagg 1680
```

```
     ggagtaatat ctcaaacaaa taat-
taaaaa actcctttaa atgtggctat aaatacctga   1740
aaccaatcct tctttcctca act-
caaatct tcaatcttta gatcatctct ccaaaaaaat  1800
atggcaggtt ccaacgtttt cattt-
taata gcttgcttca ttttgttggg tttttcaagt    1860
atggaggtta gcctagcaac tc-
gaaatatt cagcacgtgt cactaattga agtgtcacca 1920
ataacattgt cgttattccc accattgc-
ca ccaataagat ctccgttctt gccaccaata       1980
ccaccaataa cattgtcacc aatgacat-
tg gcaccaataa cattgacacc aacaggtaca       2040
ccaatcgagg aaccaataga tccac-
caacc gagaaaccaa cagatccacc aactgaggta    2100
ccaacactgc cttgaatccc aaagctac-
ca acaatcccac catcttagcc taagcctatc       2160
actgttcttc cacaagttcc cagcaat-
agc ttgccttcca ttcctttcat gtctccatct      2220
ccacctccac ctccacctcc atccagc-
tat tgaagacaat ttgattccta attagtatca      2280
catatattac tgagaatgaa ctctgt-
catc acattctcta tgatgttatt tcatgaaata     2340
agaatgtagt ttctatttac atttta-
cata tataataaag tgtggtgttt tttttaagtt     2400
attaaattat taaaattata tatc-
caaaaa tataaacatg attaaatgtt atacaatcat   2460
ttataaaggt attataattg atgctat-
caa ctccaacata gttatacttc aggaaaaaaa      2520
aacataacat aatcacttgc caatgaat-
ga tgtgattatt ttaggtataa ttgcaaaaaa       2580
atcctcaacg tttggggact tttg-
gttttg tgcctttgac ctttttttta ttgacaccct   2640
caacattata atttttttc agaaatt-
agc ctaattttaa caataaatgt gagttaaccg      2700
ttaatcaagc gccgatcaac-
gaaataagtc tatgtggcat accacataag cacgatgaca 2760
tcatctaaaa aattgtttaa-
caattttttt ttttcatttt gtttccttct ttcttcttct 2820
ctctttctct cttcctgcta tta-
cag                                        2846
```

A promoter fragment of 1378 bp (SEQ ID NO: 2) was amplified from BAC4A23 using the primers gwSCWPRP_F
1 ggggacaagt_ttgtacaaaaaagcaggcta_tagtatgaga_ tgatctat-tgattctatatt 60
    ctta 64
(SEQ ID NO: 16) and gwSCWPRP_R
1 gggaccactt_tgtacaagaa_agctgggtat_tttttggag_agatgatcta_aagattgaag 60
att 63

(SEQ ID NO: 17). The amplification product was cloned by the BP in vitro recombination reaction (Invitrogen) into pDONR201 and confirmed by sequencing. This was recombined into the SirogateIV-GUS expression vector by the LR reaction (Invitrogen) to produce the construct 4A23promoter/Sirogate IV GUS, confirmed by sequencing and introduced into the AGL1 strain of *Agrobacterium tumefaciens* for introduction into cotton cells by *Agrobacterium*-mediated transformation.

SEQ ID NO: 2

```
  1 atagtatgag atgatctatt gattc-
tatat tcttaccgtt gaatttatga atttttttc     60 ttatttcttt tgagtttgat taatgatg-
ta ctgtatttat atgtttatcg aagaatattt      120
tatatttaaa atttatttaa tctcatt-
agt tgatacttgt ctttttgtt cttcacggaa      180
```

```
-continued
  agttgttata tataagttca g-
taaataata atgaaatata aattttaatt atatctagta    240
ctcaataaga agatggagaa agttatgt-
ta attatagtta taaattattt ataaatttaa           300
tatatatata taaagaaaat agttg-
tataa ctaataatta tttttacaat actttatata        360
gttatattta aaaaaatttt aaaat-
taaaa tactattatt ttgttcaata tattaatatt        420
tatattattt aatttattat tgaatat-
gaa taaattttt ttgaaaatta tatttttaat           480
ttttagaaat tttatataac tttc-
catata tatatttctg atttgtcaat ttcttttgag       540
atttatctaa attgatttga attttttt-
ta tttttaaaaa ataaaataat tttaaaattt           600
cttggaattt tatataaatt tttg-
gatttt tcaaaaaaaa ttgagatttt tttctttttt       660
ttcgattttt taaatttatt tcag-
gaaaat ataaactaac ttttcttttgc tttgggtata      720 attaatatta gataacccac aaatta-
gatc aataggagct tcatgtccta atcccattta         780
attacttttg ttgtatcatt aatt-
tagtcg accttacata gtagctctat ggggcaaata       840
gttataaatg ttaaattagt att-
taaatct tgaagttttt aatttaaagt tcagactatt      900
agtattatat caaatattta aggg-
taaata tatattctaa tatctaagct tgggtcaagg       960
tttaaattaa gtacttaaac ttggttt-
tat agttcaaatt gatttaaata actaagtatt         1020
aatttgaatt aagaagcaaa gttcaag-
tac ctaattagac tataaaaaaa acttttgcta         1080
gtaaattgaa ccttaaagtc gagtt-
tagtt atctaattgg acaaaaaaat cttaaatacc       1140
aatttaaacc ctaaagtcaa gtttagg-
tac caaagtgtat atttatctaa tatttaaatt         1200
tgatccacct aatttaaatt tttttg-
gtcc aatgcaataa gagaattaat taatacttac        1260
acacatgata gagatatacc cacaaca-
gat acacactaca aaaaacatta aaaaatagaa         1320
agatatattt cctacaaaat ttaaaag-
cat ttaatttttt aactaacatt agacaaatgg         1380
aaatggaaag acttattttt aagtt-
tatgg atgaatctaa tttatctaaa cattgggttt       1440 ttttttttg tgacgaaata tgggt-
gagag aaggtagtaa gctaagtagg ggagtaatat       1500
ctcaaacaaa taattaaaaa actcctt-
taa atgtggctat aaatacctga aaccaatcct         1560
tctttcctca actcaaatct tcaatctt-
ta gatcatctct ccaaaaaaat                     1610
```

In a first step, the functionality of the promoter in the construct was tested in a transient expression assay by particle bombardment of pSirogateIV-4A23Promoter-GUS DNA into cultured cotton ovules and staining for GUS enzyme activity according to the method of Jefferson et al (1987) *EMBO J.* 6: 3901-3907.

In this experiment an expression vector comprising a 35S promoter-GUS cassette was used as a control. The activity of the promoter was monitored by counting the number of GUS spots/number of ovules analyzed (see Table 3).

TABLE 3 number of GUS spots/number of ovules analyzed.
The SCWPRP promoter was observed to drive GUS
expression between 16 dpa and 29 dpa.

| promoter | 7 dpa | 16 dpa | 29 dpa |
|---|---|---|---|
| 35S | 10/40 | 1/10 | not tested |
| SCWPRP | not tested | 5/30 | 4/28 |

In a next step cotton transformation was carried out with the *Agrobacterium* strain carrying pSirogateIV-4A23 promoter-GUS essentially as described in Murray et al. (1999) *Mol. Breed.* 5: 219-232, using the seedling cotyledon segments of cotton cultivar Coker315-11 as a source of cotton tissue in the transformation. Coker315-11 is a CSIRO selection from the regenerable Coker 315 cultivar. In the transformation experiment, selection was carried out for resistance to kanamycin sulphate.

Figure 4:
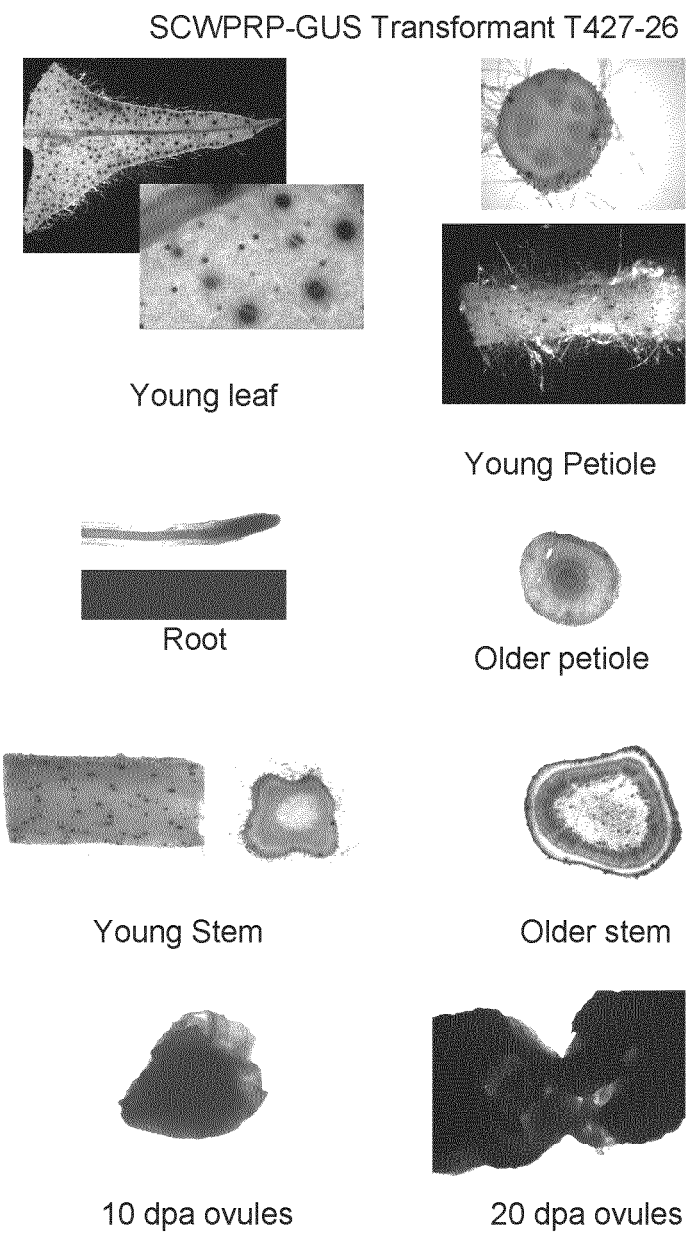
FIG. 4: GUS staining patterns for a representative transformant containing the SCWPRP promoter-GUS construct. It is noted that there is weaker staining in 10 dpa fiber and a very strong staining in 20 dpa fibers. There was also strong staining in a glandular trichome on the surface of leaves, petioles and stems, but no staining was observed in vegetative trichomes.

A total of 17 primary transformants were generated representing 12 independent transformation events. The transformed plants were transferred to soil and allowed to flower. Flowers were tagged at anthesis. Both 10 and 20 dpa bolls were collected and whole seeds with fibers stained for GUS enzyme using X-gluc histochemical stains as described by Jefferson et al., 1987. Immature leaves, petiole segments, roots and stem sections from both young and older branches were also stained for GUS. Staining patterns are summarized in Table 4 and representative images in FIG. 4.

TABLE 4

| Transformant line | Leaf | Petiole | Stem | Root | 10 dpa fiber | 20 dpa fiber |
|---|---|---|---|---|---|---|
| T427-26 | + Only in small surface glands- not in trichomes | + Only in small surface glands- not in trichomes; some weak staining in centre of older petioles | + Only in some surface glands- not in trichomes | − | ++ | +++ |
| T427-6-1 | + Only in small surface glands- not in trichomes | + Only in small surface glands- not in trichomes | + Only in small surface glands- not in trichomes | − | ++ | +++ |

Tissues in which GUS enzyme activity was detected in different $T_0$ transgenic cotton plants transformed with the SirogateIV-SCWPRP promoter-GUS construct. +, weak or localized expression, ++ medium expression, +++ very strong expression, − no staining.

The SCWPRP promoter was observed to be selectively expressed in fibers particularly at later stages in agreement with the Q-PCR data. It was also expressed in some sort of a glandular trichome present on most green epidermal surfaces of above-ground tissues.

Materials and Methods
1. Cotton Ovule Culture and Particle Bombardment

Cotton bolls from each fiber initiation stage were harvested, surface-sterilized in 95% ethanol, flamed briefly, and dissected under sterile conditions. Ovules were transferred to a liquid culture medium in the presence of 5 µM indole-3-acetic acid and 0.5 µM gibberellic acid. The ovules were placed on 2 Whatmann filter papers pre-moistened with Medium 100 (MS salts, B5 vitamins, MES 0.5 g/l, $MgCl_2.6H_2O$ 0.94 g/l, gelrite 2 g/l, glucose 30 g/L, pH 5.8) supplemented with 0.2 M mannitol before bombardment. DNA was precipitated onto 1 µm gold particles by the calcium chloride-spermidine method described in the BioRad (Richmond, Calif.) instruction manual for the Biolistic Particle Delivery System (1000/he). Cultured ovules were bombarded with a 6, 9 and 12 cm target distance in 28 inch Hg vacuum according to the manufacturer's recommendation for plant tissues and with various Helium pressures (900 and 1350 psi). The bombarded ovules were transferred immediately to a fresh liquid medium or were incubated on a solid medium for 2 days before transfer to a liquid medium. A single layer of Micropore surgical tape (3M Healthcare, St. Paul, Minn.) was used to seal each dish to prevent drying out of the tissues. Cultures were incubated at 32° C. in a 5% $CO_2$ atmosphere. Each construct was bombarded into more than 120 ovules per replicate and the experiments were repeated at least 6 times.

2. Analysis of Beta-Glucuronidase Expression Patterns

Histochemical localization of GUS enzyme activity was carried out using the substrate 5-bromo-4-chloro-3-indolyl-beta-D-glucuronide (X-Gluc) as described by Jefferson R A et al (1987) EMBO J. 6: 3901-3907. To prevent diffusion of the GUS product during staining, 0.5 mM of potassium ferri/ferrocyanide was added to the histochemical staining buffer. Pictures of histochemically stained ovules associated with fibers were taken with an Olympus SZX stereomicroscope with an Olympus DP11 digital camera. Image composites were constructed using Adobe Photoshop 5.5 software.

Example 2

Expression of the FS18 Promoter in Cotton Plants

Primary cotton transformants were generated as described in example 1 with a construct comprising a chimeric gene for expression GUS under control of the FS18 promoter (pSirogateIV-FS18(3P22)GUS). T1 seeds from four independent primary transformants with high expression in 10 or 20 dpa fiber were collected and planted in the glasshouse. These lines were T420-24, T420-31, T420-37 and T420-48. Sections of cotyledons were stained with X-Gluc as previously described. Gus activity was observed in many of the plants in small glandular trichomes distributed across the cotyledon and in areas around cut edges indicating a wound response. When whole cotyledons were stained GUS activity was only observed in the glandular trichomes and in some patchy areas near edges or internally on the cotyledon presumably in areas that had been damaged during handling prior to staining or when watering plants. Not all cotyledons had this diffuse staining in patches.

Two T1 plants from each line were grown to maturity and flowers tagged to collect bolls of different ages (0, 10, 20 and 30 dpa) and various other tissues harvested including leaf, petiole, stem, root, bollcoat (at 10 and 20 dpa), small flower bud and various flower parts at 0 dpa (including flower bract, petal, stamens and stigma). These were stained for GUS activity and similar material frozen for extraction of RNA and quantitative RT-PCR to look at the relative levels of expression in different tissues. GUS staining was in X-Gluc solution overnight at 37° C. as described in example 1. Tissues were cleared in an ethanol series until no more chlorophyll was extracted and photographed. All lines had similar staining patterns. As an example, the results for line T420-24 are tabulated in Table 5 below.

TABLE 5

GUS-staining patterns for line T420-24.

| Tissue | Comment |
|---|---|
| 0 dpa ovule | Ovule surface stained |
| 10 dpa fibre and ovule | Fibres strongly stained |
| 20 dpa fibre | Fibres strongly stained |
| 30 dpa fibre | Fibres strongly stained |

TABLE 5-continued

GUS-staining patterns for line T420-24.

| Tissue | Comment |
| --- | --- |
| Cotyledon | Small glandular trichomes stained, some patchy staining of mesophyll and epidermis around wounds. A few glands around the nectary strongly stained but most glands within the nectary not stained |
| Leaf | Small glandular trichomes stained, some staining at cut edges or around damage, some hair trichomes stained, but only near areas were there is a wounding response |
| Leaf Petiole | Small glandular trichomes stained, hair trichomes not stained |
| Stem | Some weak patchy staining in vasculature, but probably a wound response in cut sections |
| Root | No staining |
| Boll Coat (0, 10 and 20 dpa) | Staining of the bollcoat wall and septum separating locules at all stages |
| Flower bud | A few small glandular trichomes stained but not hair trichomes, occasional staining of damaged areas. |
| Flower Bract | A few small glandular trichomes stained, but not hair trichomes. |
| Petal | Staining of small glandular trichomes at the base of the petal and only along one edge where the petals overlap. Some patchy staining of damaged areas of petal particularly more distal to the base of the petal where staining could be quite strong. |
| Stamen/Anther/Pollen | Very strong staining in pollen, weaker staining of anther wall and some times the filament |
| Stigma/Style | Weak staining of the stigma surface and stigmatic papillae |

Quantitative GUS Expression in Different Tissues

Samples were collected and RNA prepared as described in Wan and Wilkins (1994) (*Anal Biochem* 223: 72-12) and DNAase treated. Total RNA was converted to cDNA using Superscript II Reverse transcriptase and random primers and Quantitative RT-PCR carried out as described previously. Primers used were Q-GUS (SEQ ID NO: 24)
   1                 CAGGGAGGCA_AACAATGAAT_CAA-CAACTCT_C 31
   and Q-ME (SEQ ID NO: 25)
   1                 TGCAAACAGC_AACAGATCAA_CTGTC-CTTTT_TCC 33
specific to the introduced GUS transgene and the endogenous cotton ubiquitin gene used for normalization as previously described. All samples were adjusted relative to the expression of GUS in each plant of 30 dpa fibres set as 1.0 and then averaged across two different plants in each of four different independent lines.

Figure 5A:
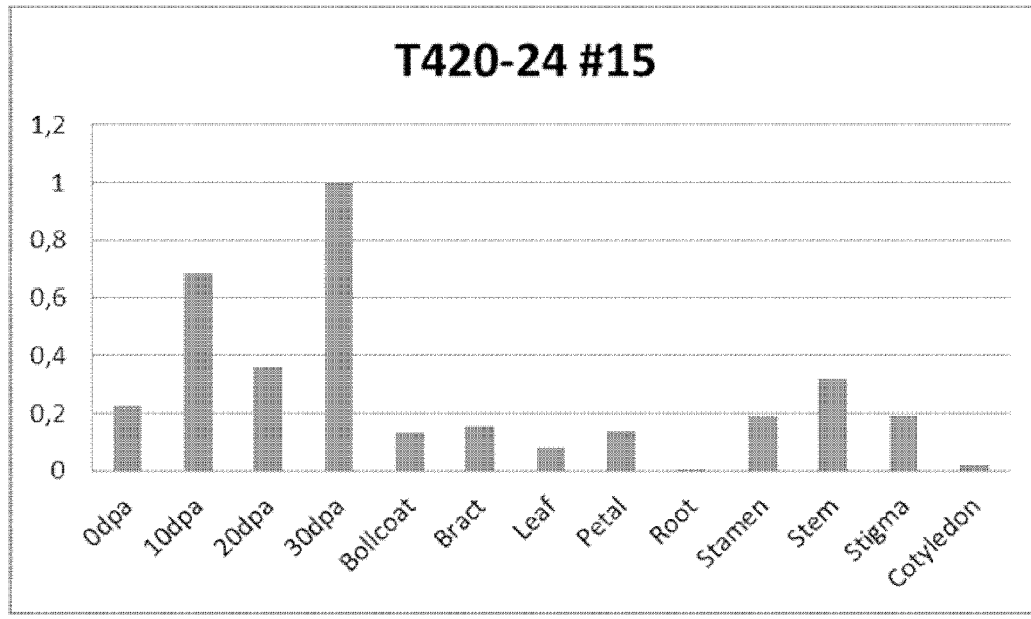
FIG. 5: Expression of the GUS transcript driven by the FS18 promoter in different tissues of cotton. Data for two different T1 plants for each of four different independent lines (FIG. 5A to 5D) are given with expression relative to the 30 dpa fiber sample. Quantitative data is given in FIG. 5E. In leaves, there were two outliers (highlighted) which are suspected to be due to thrips damage of the leaves prior to sample collection. Nd: not determined.
Figure 5A:
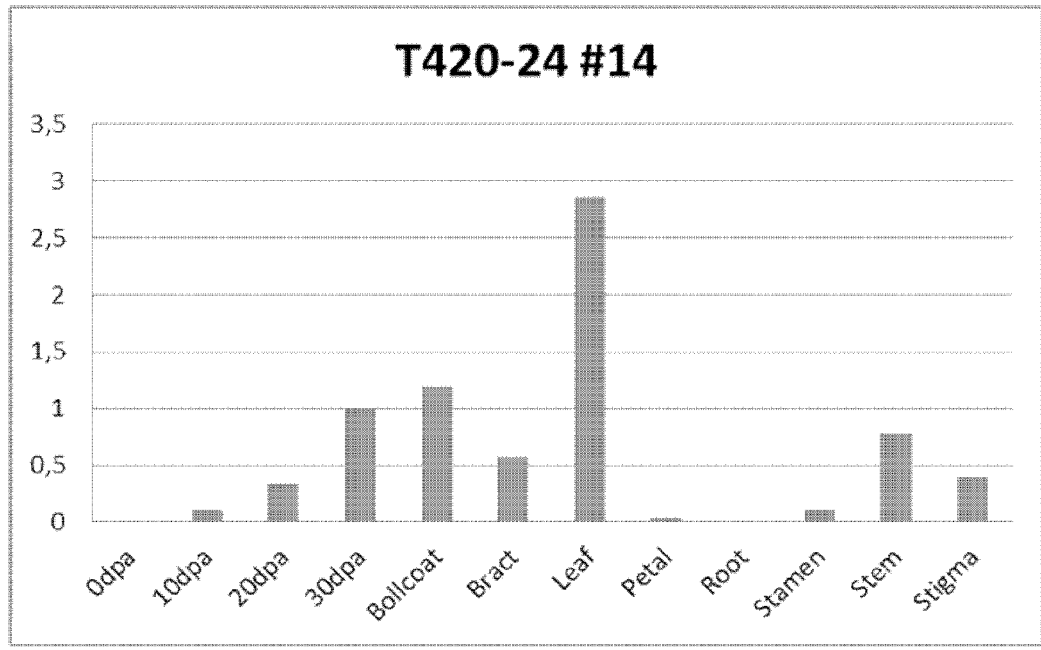
Figure 5B:
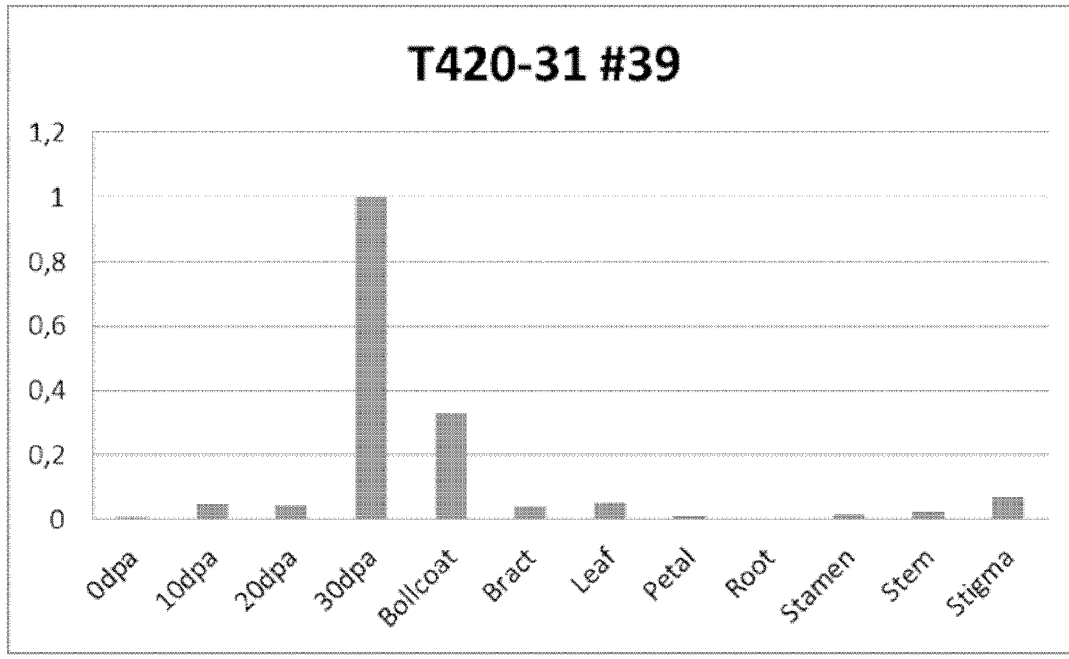
Figure 5B:
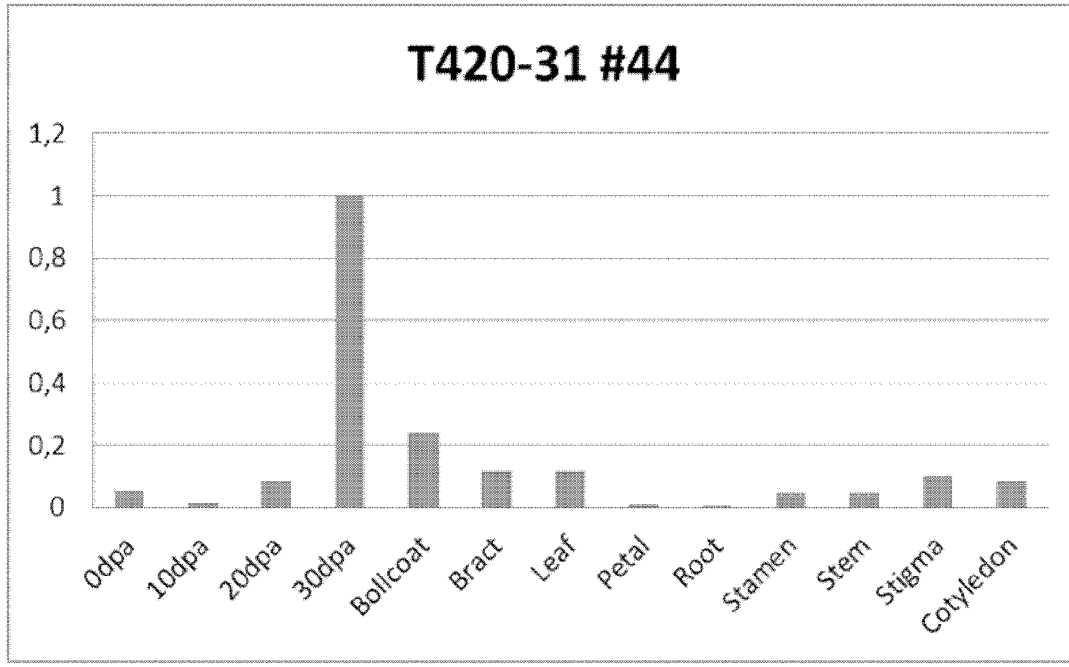
Figure 5C:
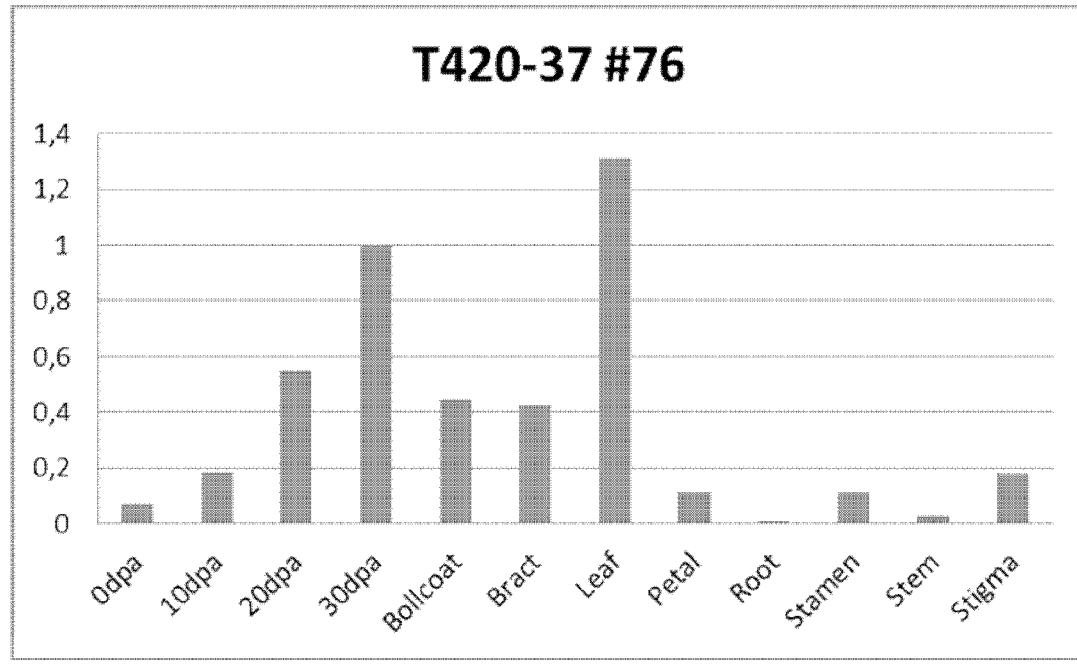
Figure 5C:
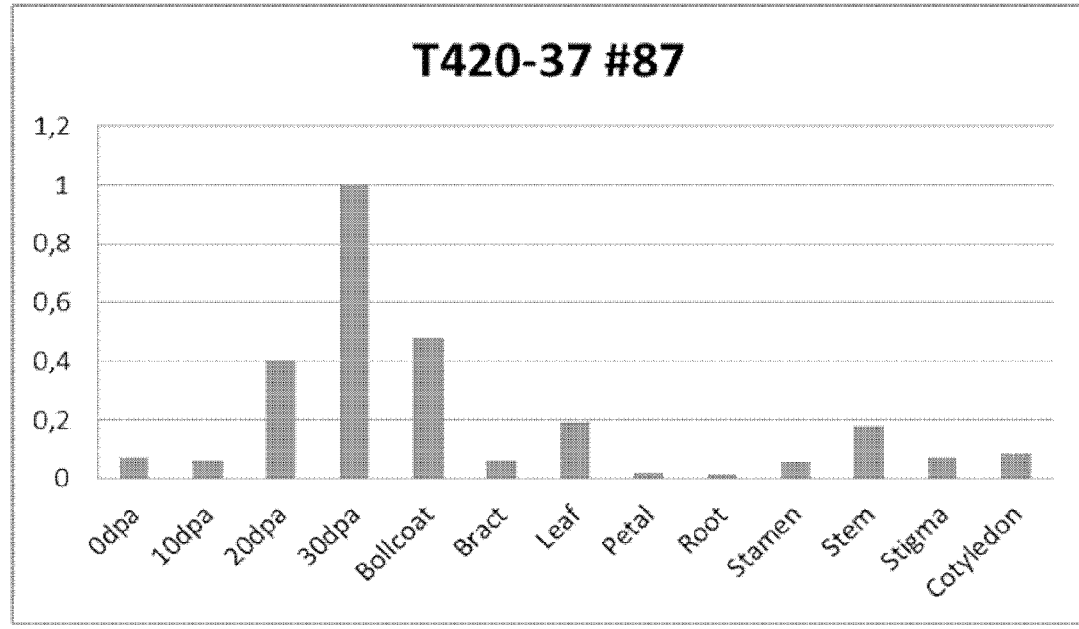
Figure 5D:
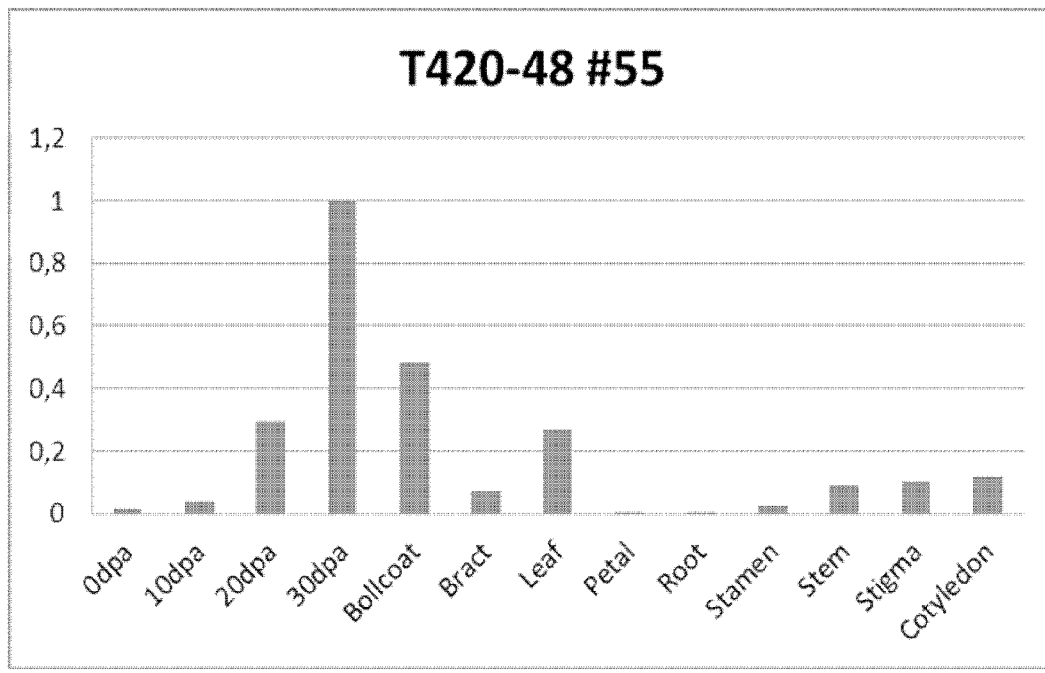
Figure 5D:
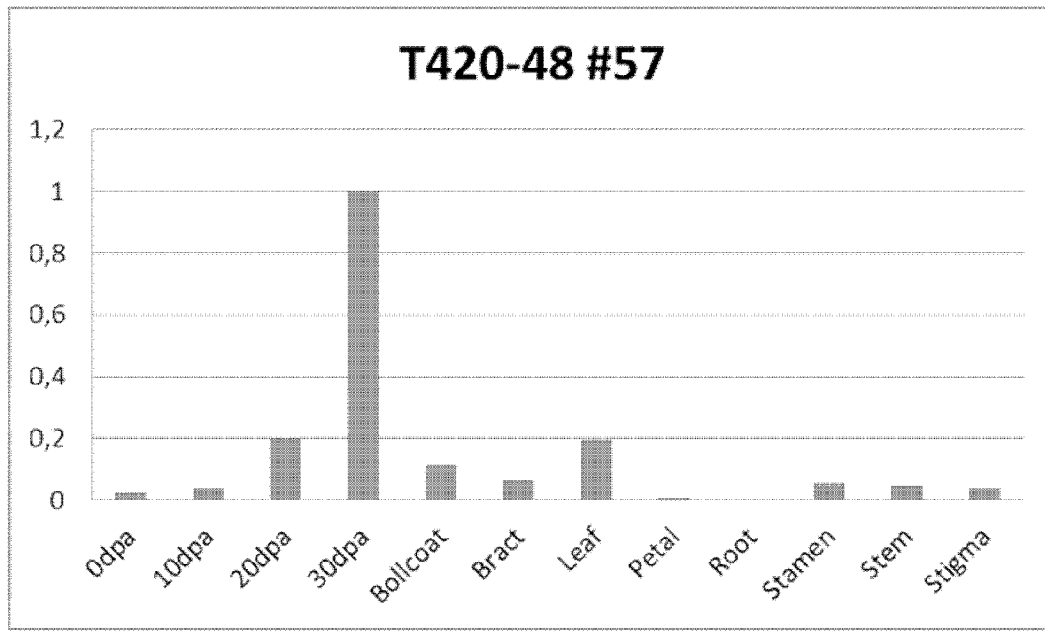

Q-PCR indicates that the FS18 promoter is active throughout fiber development, but is more strongly expressed later in development. Consistent with the GUS staining data the promoter appears to be active in the bollcoat and leaf (probably in response to insect damage as it was quite variable with most samples having little or no GUS expression in leaves). Expression in other tissues was low as the small glandular trichomes where GUS was detected by staining represent a very small proportion of the total cells extracted. High GUS transcripts were not detected in the stamens. An overview of expression in different tissues is given in FIG. 5, the quantitative data on this experiment can be taken from FIG. 5E.

Conclusion

Overall, these data support the conclusion that the FS18 promoter is fiber-preferential and expressed throughout fiber development, but is more active during the later stages of secondary cell wall deposition. It is expressed elsewhere in the plant, but usually in relatively specialised cells or tissues, including small glandular trichomes distributed throughout the plant epidermis on stems, leaves, bracts, petioles and petals. There is some expression in the maternal bollcoat. The promoter also has some wound responsiveness, but this appears to be a minor activity.

Example 3

Expression of the SCW-PRP Promoter in Cotton

T1 seeds from four independent primary transformants were generated according to the method of example 1 with a construct comprising a chimeric gene for expression GUS under control of the SCW_PRP promoter (SirogateIV-SCW-PRP promoter-GUS construct) and transformants with high expression in 10 or 20 dpa fibre were collected from primary transformants generated according to the method described in example 1 and comprising a chimeric gene for expression GUS under control of the SCW-PRP promoter and planted in the glasshouse. These lines were T427-5, T427-6, T427-26-1 (introduced in example 1) and T427-31. Sections of cotyledons were stained with X-Gluc, as previously described. Gus activity was observed in many of the plants in small glandular trichomes distributed across the cotyledon and in areas around cut edges indicating a wound response. When whole cotyledons were stained GUS activity was only observed in the numerous glandular trichomes across the cotyledon and its petiole and in some patchy areas near edges or internally on the cotyledon presumably in areas that had been damaged during handling prior to staining or when watering plants. Not all cotyledons had this diffuse staining in patches.

Two plants from each line were grown to maturity and flowers tagged to collect bolls of different ages (0, 10, 20 and 30 dpa) and various other tissues harvested including leaf, petiole, stem, root, bollcoat (at 10 and 20 dpa), small flower bud and various flower parts at 0 dpa (including flower bract, petal, stamens and stigma). These were stained for GUS activity and similar material frozen for extraction of RNA and quantitative RT-PCR to look at the relative levels of expression in different tissues. GUS staining was in X-Gluc solution overnight at 37° C., as described previously. Tissues were cleared in an ethanol series until no more chlorophyll was extracted and photographed. All lines had similar staining patterns. The results for line T427-5 are depicted in table 6 below.

TABLE 6

GUS-staining patterns for line T427-5

| Tissue | Comment |
| --- | --- |
| 0 dpa ovule | Ovule surface stained |
| 10 dpa fibre and ovule | Fibres strongly stained |
| 20 dpa fibre | Fibres strongly stained |
| 30 dpa fibre | Fibres strongly stained |
| Cotyledon | Numerous small glandular trichomes along small and large veins and in and around the nectary were stained (more than with FS18GUS), some patchy staining of mesophyll and epidermis around wounds (stronger than FS18GUS) |
| Leaf | Numerous small glandular trichomes stained, some staining at cut edges or around damage, some hair trichomes stained but only near areas were there is a wounding response |

TABLE 6-continued

GUS-staining patterns for line T427-5

| Tissue | Comment |
| --- | --- |
| Leaf Petiole | Small glandular trichomes stained, hair trichomes not stained |
| Stem | Some weak patchy staining in vasculature, but probably a wound response in cut sections |
| Root | No staining |
| Boll Coat (0, 10 and 20 dpa) | Staining of the inner bollcoat wall and septum separating locules at all stages |
| Flower bud | A few small glandular trichomes stained but not hair trichomes, occasional staining of damaged areas. |
| Flower Bract | A few small glandular trichomes stained, but not hair trichomes. |
| Petal | Staining of small glandular trichomes at the base of the petal stained intensely along one edge where the petals overlap. Occasional patchy staining of damaged areas of petal |
| Stamen/Anther/Pollen | Very strong staining in pollen, weaker staining of anther wall and sometimes the filament |
| Stigma/Style | Weak staining of the stigma surface and stigmatic papillae |

Samples were collected and RNA prepared as described in Wan and Wilkins (1994) (Anal Biochem 223: 72-12) and DNAase treated. Total RNA was converted to cDNA using Superscript II Reverse transcriptase and random primers and Quantitative RT-PCR carried out as described previously. Primers used were Q-GUS (SEQ ID NO: 24)
1   CAGGGAGGCA_AACAATGAAT_CAACAACTCT_C 31
and Q-ME (SEQ ID NO: 25)
1              TGCAAACAGC_AACAGATCAA_CTGTC-CTTTT_TCC 33
specific to the introduced GUS transgene and the endogenous cotton ubiquitin gene used for normalization as previously described. All samples were adjusted relative to the expression of GUS in each plant of 30 dpa fibres set as 1.0 and then averaged across two different plants in each of four different independent lines.

Figure 6A:
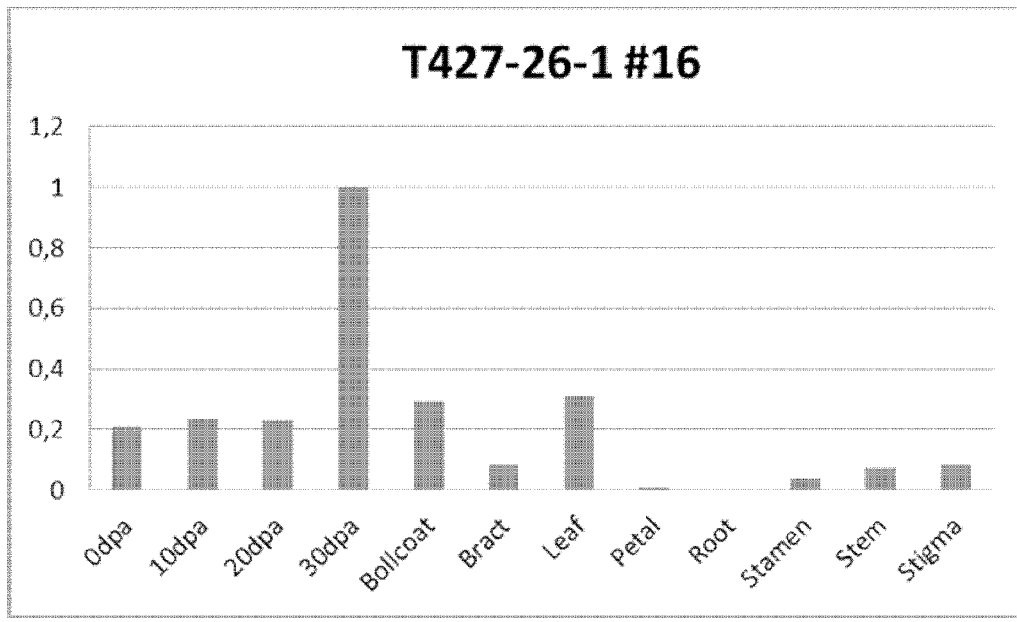
FIG. 6: Expression of the GUS transcript driven by the SCW-PRP promoter in different tissues of cotton. Data for two different T1 plants for each of four different independent lines (FIG. 6A to 6D) are given with expression relative to the 30 dpa fiber sample. Quantitative data is given in FIG. 6E. Nd: not determined.
Figure 6A:
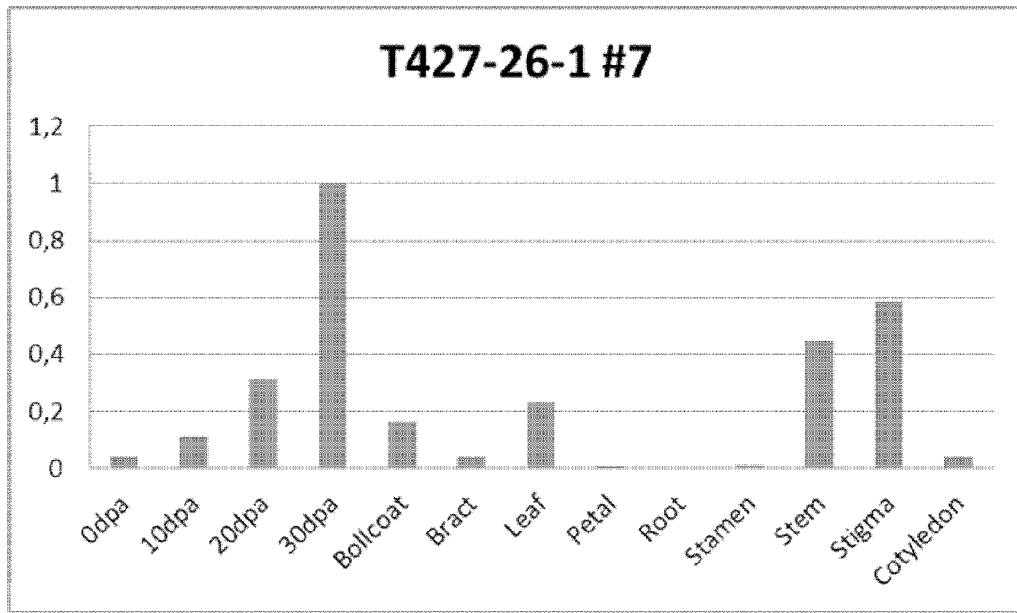
Figure 6B:
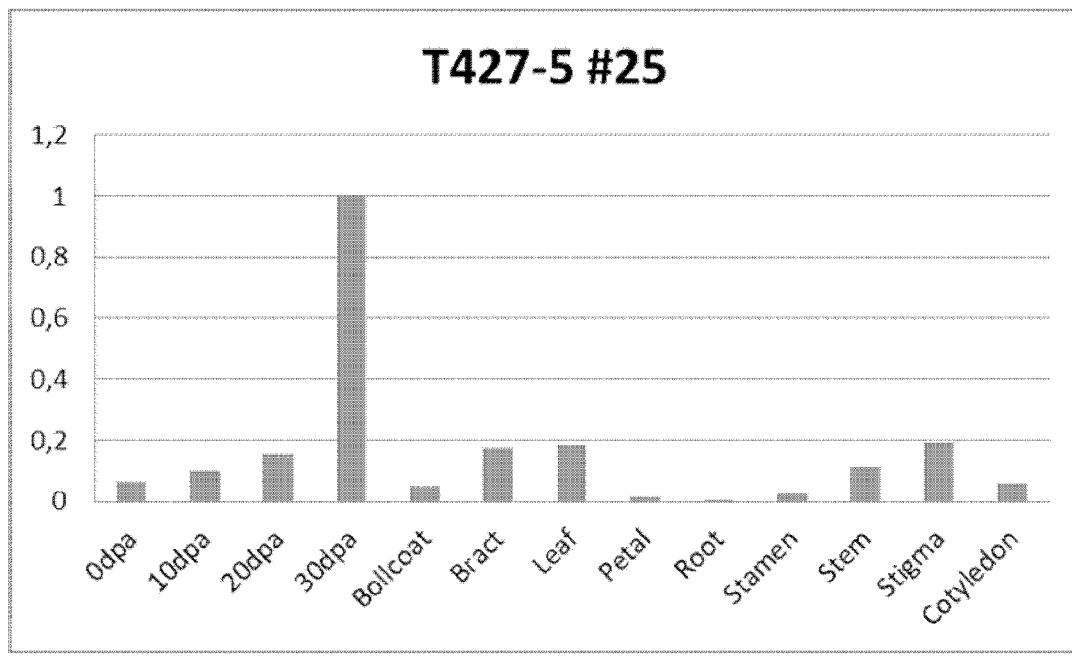
Figure 6B:
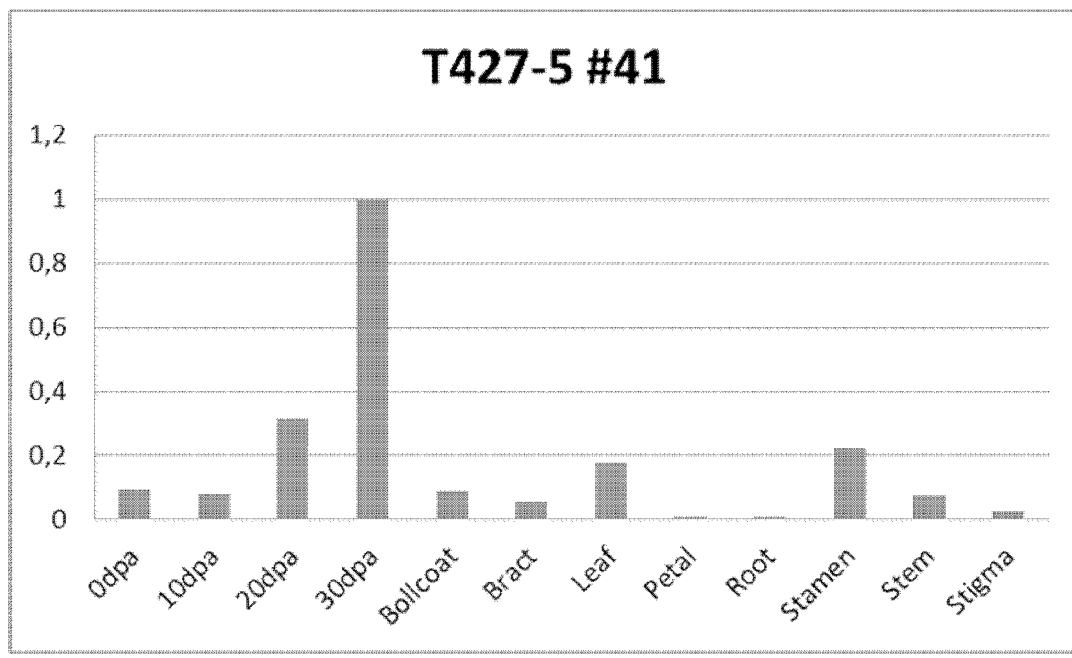
Figure 6C:
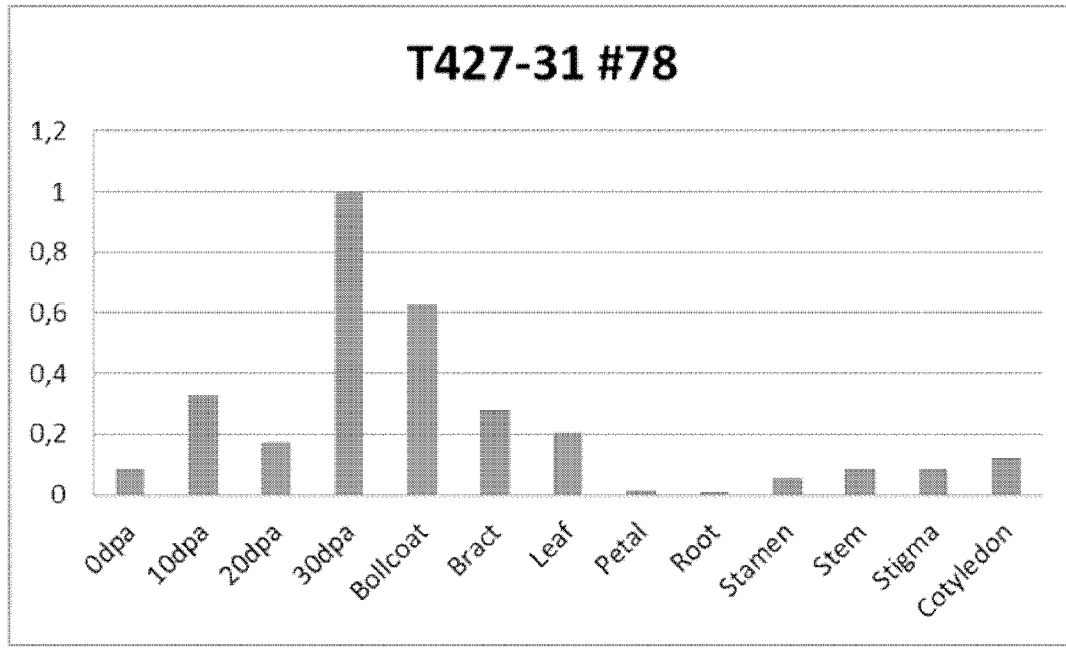
Figure 6C:
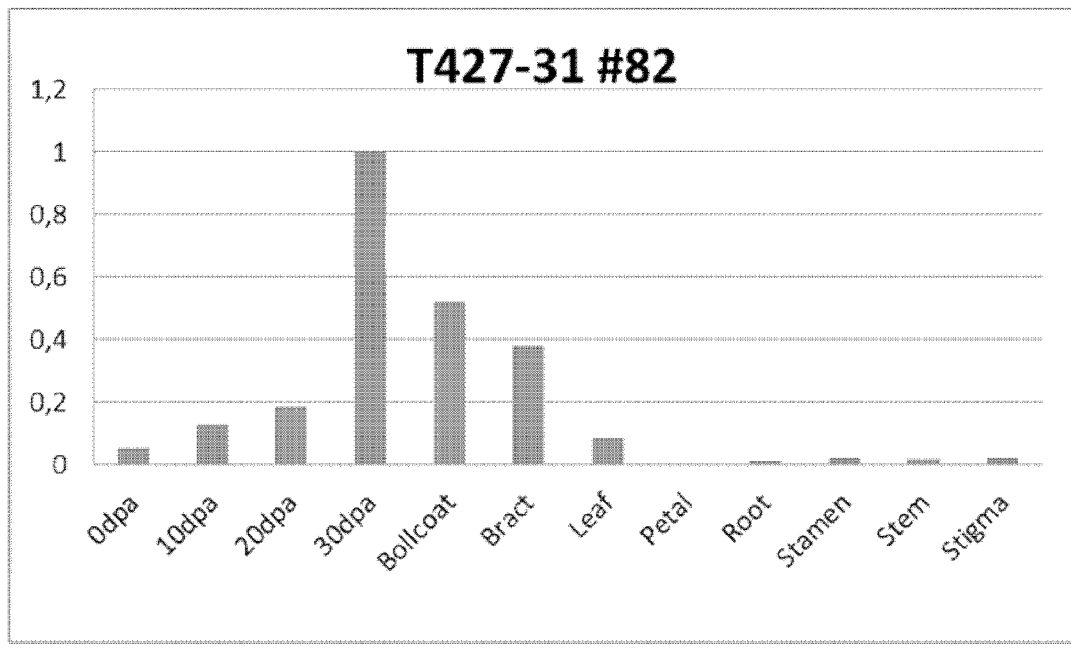
Figure 6D:
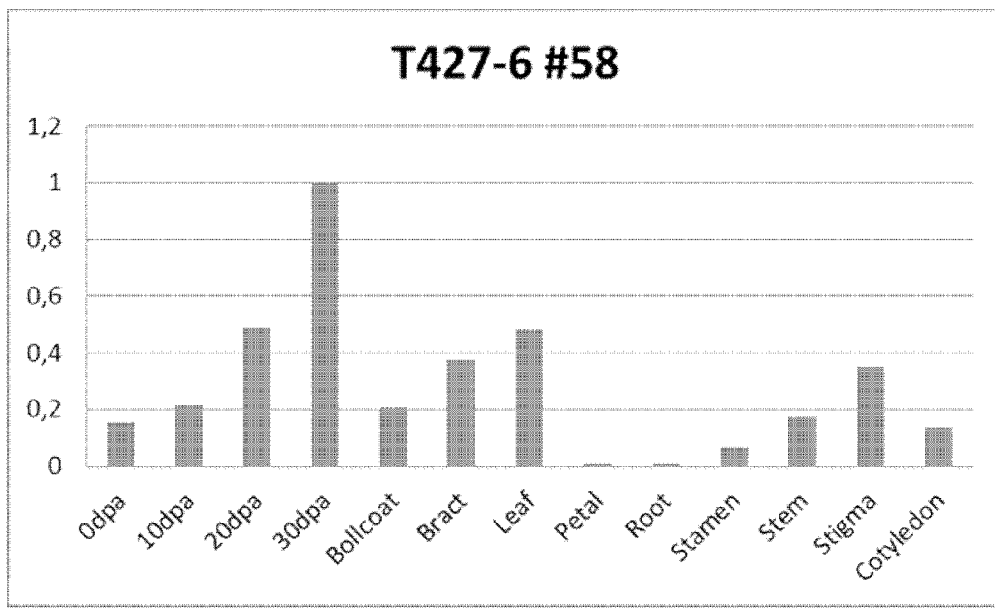
Figure 6D:
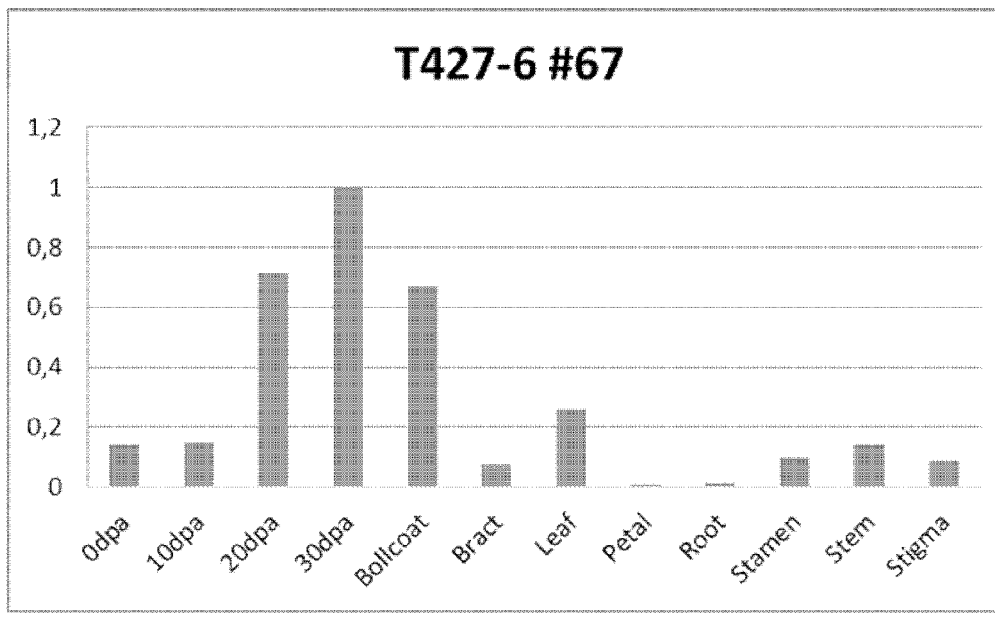

Q-PCR indicates that the SCW-PRP promoter is active throughout fibre development, but is more strongly expressed later in development. Expression in other tissues was low as the small glandular trichomes where GUS was detected by staining represent a very small proportion of the total cells extracted. The SCW-PRP promoter appears to be active in more glandular trichomes than is the FS18 promoter High levels of GUS transcripts were not detected in the stamens. An overview of expression in different tissues is given in FIG. 6, the quantitative data on this experiment can be taken from FIG. 6E.

Conclusion

Overall, these data support the conclusions drawn from the earlier studies that the SCW-PRP promoter is fibre-preferential and expressed throughout fibre development, but more active during the later stages of secondary cell wall deposition. It is sometimes expressed elsewhere in the plant, but usually in relatively specialised cells or tissues, including small glandular trichomes distributed throughout the plant epidermis on cotyledons, stems, leaves, bracts, petioles and petals. There is some expression in the inner walls of the maternal bollcoat. The promoter also has some wound responsiveness, but this appears to be a minor activity.

Example 4

Expression of Chitin Synthase Under Control of the FS18 and SCW-PRP Promoters in Cotton Chitin synthases can be expressed in cotton plants to increase positive charges in the cotton fiber by introducing chitin polymers into the fiber cell wall. For this, fiber-preferential or fiber-specific expression is important since plants transformed with a chitin synthase gene mostly do not show an appreciable phenotype if the promoter controlling expression of the chitin synthase is driving expression in many other tissues or cell types than fiber cells.

Four vectors comprising chimeric genes according to the invention were generated:

pTIB344: comprises a nucleic acid sequence encoding the *Neurospora crassa* chitin synthase 2 gene (Din and Yarden, 1994, SEQ ID NO: 19) comprising a Golgi-targeting signal from *Arabidopsis thaliana* (Pagny et al., 2003, SEQ ID NO: 20) under control of the FS18 promoter and the epsps gene (double mutant of the 5-enol-pyruvylshikimate-3-phosphate synthase gene of *Zea mays*, Lebrun et al., 1997; SEQ ID NO: 21) as selectable marker gene.

pTIB345: comprises a nucleic acid sequence encoding the *Neurospora crassa* chitin synthase 2 gene comprising a Golgi-targeting signal under control of the SCW-PRP promoter and epsps as selectable marker gene.

These vectors were used for transforming cotton variety Coker312-17 using a hypocotyl transformation method known in the art. For pTIB344 17 out of 61 plants and for pTIB345 16 out of 67 plants showed good plant development. 6 (pTIB344) and 1 (pTIB345) plants have set bolls so far indicating that potential expression of chitin synthase in the bollcoat does not prevent the plants from setting bolls.

pTIB328: comprises a nucleic acid sequence encoding the *Neurospora crassa* chitin synthase comprising a Golgi-targeting signal under control of the FS18 promoter and the bar gene (phosphinotricin acetyltransferase gene of *Streptomyces hygroscopicus* (Thompson et al., 1987; SEQ ID NO: 22) as selectable marker gene.

pTIB329: comprises a nucleic acid sequence encoding the *Neurospora crassa* chitin synthase comprising a Golgi-targeting signal under control of the SCW-PRP promoter and bar as selectable marker gene.

These vectors were used for transforming cotton variety Coker312-17 in a callus transformation method known in the art. For pTIB328 1 and for pTIB329 5 T0 plants has produced seeds so far indicating that potential expression of chitin synthase in the bollcoat does not prevent the plants from setting bolls and producing seeds.

All of these vectors, in addition to what is listed above, express the gfa (glutamine:fructose-6-phosphate amidotransferase) gene from *E. coli* (Frohberg and Essigmann, 2006; SEQ ID NO: 23) under control of the same promoter than the chitin synthase gene to further increase chitin provision to the cells.

The invention claimed is:

1. A chimeric gene comprising the following operably linked DNA regions a) a nucleotide sequence of a fiber cell preferential or selective promoter comprising the nucleotide sequence of SEQ ID NO: 1 or SEQ ID NO: 2, which drives expression throughout fiber development and is more active during the later stages of secondary cell wall deposition;
b) a heterologous DNA region; and
c) optionally a transcription termination and polyadenylation signal.

2. The chimeric gene according to claim 1, wherein said heterologous DNA region encodes a protein of interest.

3. The chimeric gene according to claim 1 wherein said heterologous DNA region encodes a ribozyme, microRNA, double stranded hairpin RNA or antisense RNA.

4. A recombinant vector comprising a chimeric gene according to any one of claims 1 to 3.

5. A plant cell comprising a chimeric gene according to any one of claims 1 to 3.

6. A plant comprising in its cells a chimeric gene according to any one of claims 1 to 3.

7. A plant according to claim 6, wherein the plant has altered fiber, wherein said fiber is altered in composition, length or strength.

8. The plant according to claim 6, which is a cotton plant.

9. A seed of a plant, said seed comprising in its cells a chimeric gene according to any one of claims 1 to 3.

10. A method for expressing a biologically active RNA preferentially in a fiber cell of a fiber-producing plant throughout fiber development and more actively during the later stages of secondary cell wall deposition said method comprising
  a. providing the cells of said plant with a chimeric gene according to any one of claims 1 to 3; and
  b. growing said plant, preferably such that said plant produces fibers.

11. The method according to claim 10, wherein said plant is a cotton plant.

12. A method of producing a transformed plant cell or plant, comprising introducing the chimeric gene according to any one of claims 1 to 3 into a parental plant cell to produce a transformed plant cell, and optionally regenerating a plant from said transformed plant cell.

13. A method of producing an altered fiber, comprising (i) growing the plant of claim 6, and (ii) harvesting the fiber from the plant.

14. An altered fiber harvested from a plant according to claim 6 comprising said chimeric gene.

* * * * *

SEQUENCE LISTING

<160> NUMBER OF SEQ ID NOS: 23

<210> SEQ ID NO 1
<211> LENGTH: 1376
<212> TYPE: DNA
<213> ORGANISM: Gossypium hirsutum

<400> SEQUENCE: 1

```
aatggatcgg gcctcgagta agaattttt ggtccgagcc caacccagat ttacaaaaaa    60
attgttgttg ttgtttttct actgttttat tgtcatttca ctattatatt gttattgttt   120
tgttgttatt atcacacggc cgtgtgtcac acataggcat gtgccttgag cgtgttgaaa   180
aatagtatag gtgtagtttc cacacggtct gacacacggt cgtgtatctc aagtcaatga   240
gttacacaga tagagacacg ggctgggata cggccatgtg tcccaacttt gaaagtcaca   300
cggcctgggg cattccacac gatcgtgtgt ctcctgtttc taggcacttt gagatttcac   360
cctaaacttc tagaattgtt tcaaattagc ccctatttgt tcttaaatca ttttagggcc   420
ctgtaaactc atatttagga ctaaatgggt aatttttact atgatttgaa tgaattagct   480
tgcattttaa ttatgattga tttgataata atgcccgtga ccctaatccg ttggcggaga   540
ggggttaggg gttttattgt tattttttag atattgtata gctcttgttt ttttgttaat   600
tttgttatta ttttaaaggc atttgtttgt taagttacac ctatcttaat gttatttctg   660
gtaggtttta tgggtgaata acccttgacc accaaatcaa tcacaagagt tcaatatttt   720 attatttta aaatgtattg aaaatcgtta atctatatat ttgcctatta ttggattaaa   780
tattcataag agtttagacc gtcgtgagac aagttagttt tatctaactg atggtcatcg   840
cacttagtta aaaagttagt ggcgcaaagc taccatgcgg tggattatga ttgaatgtct   900
ctaaatcaga atcaggatta gaaacgacgc acacttctgt tgcccgattg ccgaccccaa   960
tgacacgtgt tgtaggttta gccatctta tgaaagataa tgttttctgt tttataagta  1020
agcaactata gggggtttact tcggtacgca aattttagg ttaactattt tgggaagggc  1080
cattatgatt caattgaaag aaagttggca cacacaaat cactacatct gttttgacag  1140
agacacagcc taaaaacagc agcaaacaag cctaaaggaa tcacccaaaa acaacaacca  1200
aaagtacaga ggaaaacaaa agaatccctg ctaccaccaa gctgaaaaaa agaaaataaa  1260
aactcaactt ttggctataa aaaccctcct accctcaacc cctaaccacg caacaatcag  1320
caatactcca agcaaccatt ttccttacaa gtttgttttt cttgtgatta atccat       1376
```

<210> SEQ ID NO 2
<211> LENGTH: 1610
<212> TYPE: DNA
<213> ORGANISM: Gossypium hirsutum

<400> SEQUENCE: 2

```
atagtatgag atgatctatt gattctatat tcttaccgtt gaatttatga attttttttc    60
ttatttcttt tgagtttgat taatgatgta ctgtatttat atgttatcg aagaatattt   120 tatatttaaa atttatttaa tctcattagt tgatacttgt cttttttgtt cttcacggaa   180
agttgttata tataagttca gtaaataata atgaaatata aattttaatt atatctagta   240
ctcaataaga agatggagaa agttatgtta attatagtta taaattattt ataaatttaa   300
tatatatata taaagaaaat agttgtataa ctaataatta ttttacaat acttatata   360 gttatatttta aaaaaatttt aaaattaaaa tactattatt ttgttcaata tattaatatt   420
tatattattt aatttattat tgaatatgaa taaattttt ttgaaaatta tattttaat    480
```

```
ttttagaaat tttatataac tttccatata tatatttctg atttgtcaat ttcttttgag        540
atttatctaa attgatttga atttttttta ttttttaaaaa ataaaataat tttaaaattt        600
cttggaattt tatataaatt tttggatttt tcaaaaaaaa ttgagatttt tttctttttt        660
ttcgattttt taaatttatt tcaggaaaat ataaactaac ttttctttgc tttgggtata        720
attaatatta gataacccac aaattagatc aataggagct tcatgtccta atcccattta        780 attactttg ttgtatcatt aatttagtcg accttacata gtagctctat ggggcaaata        840
gttataaatg ttaaattagt atttaaatct tgaagttttt aatttaaagt tcagactatt        900
agtattatat caaatattta agggtaaata tatattctaa tatctaagct tgggtcaagg        960
tttaaattaa gtacttaaac ttggttttat agttcaaatt gatttaaata actaagtatt       1020
aatttgaatt aagaagcaaa gttcaagtac ctaattagac tataaaaaaa acttttgcta       1080
gtaaattgaa ccttaaagtc gagtttagtt atctaattgg acaaaaaaat cttaaatacc       1140
aatttaaacc ctaaagtcaa gtttaggtac caaagtgtat atttatctaa tatttaaatt       1200
tgatccacct aatttaaatt ttttggtcc aatgcaataa gagaattaat taatacttac       1260
acacatgata gagatatacc cacaacagat acacactaca aaaacatta aaaaatagaa       1320 agatatattt cctacaaaat ttaaaagcat ttaatttttt aactaacatt agacaaatgg       1380
aaatggaaag acttattttt aagtttatgg atgaatctaa tttatctaaa cattgggttt       1440 ttttttttg tgacgaaata tgggtgagag aaggtagtaa gctaagtagg ggagtaatat       1500
ctcaaacaaa taattaaaaa actcctttaa atgtggctat aaatacctga aaccaatcct       1560
tctttcctca actcaaatct tcaatctttα gatcatctct ccaaaaaaat                  1610
```

<210> SEQ ID NO 3
<211> LENGTH: 137
<212> TYPE: DNA
<213> ORGANISM: Artificial Sequence
<220> FEATURE:
<223> OTHER INFORMATION: sequence FS18

<400> SEQUENCE: 3

```
gatggcttag tcggcctccc acgctgcctt ccttttttgt cagggaatgg tgatggtgct         60
gatgccacag gttgctgtgc catcgtcatg aatgccttgg gatcgctctg tggtgataca        120
taggaaccga tctagct                                                       137
```

<210> SEQ ID NO 4
<211> LENGTH: 152
<212> TYPE: DNA
<213> ORGANISM: Artificial Sequence
<220> FEATURE:
<223> OTHER INFORMATION: sequence FS18A

<400> SEQUENCE: 4

```
gatggcgtag tcacccttcc acgctgcctt cctttattga tagggaatgg taatggtgct         60
gatgctgatg ttgatgcccc agcttgctgc gacatcgtca ggggtctctt gagctcgctg        120
ctctgtggtg gtgtttagga accgatctag ct                                     152
```

<210> SEQ ID NO 5
<211> LENGTH: 20
<212> TYPE: DNA
<213> ORGANISM: Artificial Sequence
<220> FEATURE:
<223> OTHER INFORMATION: primer FS18_F

```
<400> SEQUENCE: 5
ctagcttgaa atcgggttcg                                                  20

<210> SEQ ID NO 6
<211> LENGTH: 20
<212> TYPE: DNA
<213> ORGANISM: Artificial Sequence
<220> FEATURE:
<223> OTHER INFORMATION: primer FS18_R

<400> SEQUENCE: 6
ttggatccca cccttaaaca                                                  20

<210> SEQ ID NO 7
<211> LENGTH: 24
<212> TYPE: DNA
<213> ORGANISM: Artificial Sequence
<220> FEATURE:
<223> OTHER INFORMATION: primer RNAHel_F

<400> SEQUENCE: 7
agcctgatcg atatgtggag ggat                                             24

<210> SEQ ID NO 8
<211> LENGTH: 24
<212> TYPE: DNA
<213> ORGANISM: Artificial Sequence
<220> FEATURE:
<223> OTHER INFORMATION: primer RNAHel_R

<400> SEQUENCE: 8
tcaggaaggt ttggccatct tgga                                             24

<210> SEQ ID NO 9
<211> LENGTH: 49
<212> TYPE: DNA
<213> ORGANISM: Artificial Sequence
<220> FEATURE:
<223> OTHER INFORMATION: primer gwFS18Pro_F

<400> SEQUENCE: 9
ggggacaagt ttgtacaaaa aagcaggcta atggatcggg cctcgagta                  49

<210> SEQ ID NO 10
<211> LENGTH: 52
<212> TYPE: DNA
<213> ORGANISM: Artificial Sequence
<220> FEATURE:
<223> OTHER INFORMATION: primer gwFS18Pro_R

<400> SEQUENCE: 10
ggggaccact ttgtacaaga aagctgggta tggattaatc acaagaaaaa ca              52

<210> SEQ ID NO 11
<211> LENGTH: 659
<212> TYPE: DNA
<213> ORGANISM: Artificial Sequence
<220> FEATURE:
<223> OTHER INFORMATION: 659 bp consensus transcript

<400> SEQUENCE: 11
cgcggggaac tcaaatcttc aatctttaga tcatctctcc aaaaaaatat ggcaggttcc      60
aacgttttca ttttaatagc ttgcttcatt ttgttgggtt tttcaagtat ggaggttagc     120
ctagcaactc gaaatattca gcacgtgtca ctaattgaag tgtcaccaat aacattgtcg    180
```

```
ttattcccac cattgccacc aataagatct ccgttcttgc caccaatacc accaataaca    240
ttgtcaccaa tgacattggc accaataaca ttgacaccaa caggtacacc aatcgaggaa    300
ccaatagatc caccaaccga gaaaccaaca gatccaccaa ctgaggtacc aacactgcct    360
tgaatcccaa agctaccaac aatcccacca tcttagccta agcctatcac tgttcttcca    420
caagttccca gcaatagctt gccttccatt cctttcatgt ctccatctcc acctccacct    480
ccacctccat ccagctattg aagacaattt gattcctaat tagtatcaca tatattactg    540
agaatgaact ctgtcatcac attctctatg atgttatttc atgaaataag aatgtagttt    600
ctatttacat tttacatata taataaagtg tggtgttttt tttaaaaaaa aaaaaaaaa     659
```

```
<210> SEQ ID NO 12
<211> LENGTH: 20
<212> TYPE: DNA
<213> ORGANISM: Artificial Sequence
<220> FEATURE:
<223> OTHER INFORMATION: primer SCWPRP_F

<400> SEQUENCE: 12
caggtacacc aatcgaggaa                                                 20

<210> SEQ ID NO 13
<211> LENGTH: 20
<212> TYPE: DNA
<213> ORGANISM: Artificial Sequence
<220> FEATURE:
<223> OTHER INFORMATION: primer SCWPRP_R

<400> SEQUENCE: 13
atggtgggat tgttggtagc                                                 20

<210> SEQ ID NO 14
<211> LENGTH: 20
<212> TYPE: DNA
<213> ORGANISM: Artificial Sequence
<220> FEATURE:
<223> OTHER INFORMATION: primer SCWPRP-down

<400> SEQUENCE: 14
gcaggttcca acgttttcat                                                 20

<210> SEQ ID NO 15
<211> LENGTH: 2846
<212> TYPE: DNA
<213> ORGANISM: Artificial Sequence
<220> FEATURE:
<223> OTHER INFORMATION: sequence of BAC4A23

<400> SEQUENCE: 15
aactagtgaa acagatacaa acttgtgtta gattctacag aagtaaaaat aaattatttg     60
gggtgttaca ttgttaatat tttaaacata atcataagtt taaggaccta tctaaaatta    120
gaccaataaa atttaaaata taaatatgat attgttcttt ggatttatag aataatggat    180
tgttatatac atagtatgag atgatctatt gattctatat tcttaccgtt gaatttatga    240 atttttttc ttatttcttt tgagtttgat taatgatgta ctgtatttat atgtttatcg     300
aagaatattt tatatttaaa atttatttaa tctcattagt tgatacttgt cttttttgtt    360
cttcacggaa agttgttata tataagttca gtaaataata atgaaatata aattttaatt    420
atatctagta ctcaataaga agatggagaa agttatgtta attatagtta taaattattt    480
```

-continued

```
ataaatttaa tatatatata taaagaaaat agttgtataa ctaataatta ttttacaat    540 actttatata gttatattta aaaaaatttt aaaattaaaa tactattatt ttgttcaata    600
tattaatatt tatattattt aatttattat tgaatatgaa taaattttt ttgaaaatta    660 tattttaat ttttagaaat tttataaac tttccatata tatatttctg atttgtcaat    720
ttcttttgag atttatctaa attgatttga attttttta ttttaaaaa ataaaataat    780 tttaaaattt cttggaattt tatataaatt tttggatttt tcaaaaaaaa ttgagattt    840 ttctttttt ttcgattttt taaatttatt tcaggaaaat ataaactaac ttttctttgc    900
tttgggtata attaatatta gataacccac aaattagatc aataggagct tcatgtccta    960
atcccattta attactttg ttgtatcatt aatttagtcg accttacata gtagctctat   1020
ggggcaaata gttataaatg ttaaattagt atttaaatct tgaagttttt aatttaaagt   1080
tcagactatt agtattatat caaatattta agggtaaata tatattctaa tatctaagct   1140
tgggtcaagg tttaaattaa gtacttaaac ttggttttat agttcaaatt gatttaaata   1200
actaagtatt aatttgaatt aagaagcaaa gttcaagtac ctaattagac tataaaaaaa   1260 actttgcta gtaaattgaa ccttaaagtc gagtttagtt atctaattgg acaaaaaaat   1320
cttaaatacc aatttaaacc ctaaagtcaa gtttaggtac caaagtgtat atttatctaa   1380
tatttaaatt tgatccacct aatttaaatt ttttggtcc aatgcaataa gagaattaat   1440
taatacttac acacatgata gagatatacc cacaacagat acacactaca aaaaacatta   1500
aaaaatagaa agatatattt cctacaaaat ttaaaagcat ttaattttt aactaacatt   1560 agacaaatgg aaatggaaag acttatttt aagtttatgg atgaatctaa tttatctaaa   1620
cattgggttt ttttttttg tgacgaaata tgggtgagag aaggtagtaa gctaagtagg   1680
ggagtaatat ctcaaacaaa taattaaaaa actccttaa atgtggctat aaatacctga   1740
aaccaatcct tctttcctca actcaaatct tcaatcttta gatcatctct ccaaaaaaat   1800
atggcaggtt ccaacgtttt cattttaata gcttgcttca ttttgttggg ttttcaagt   1860 atggaggtta gcctagcaac tcgaaatatt cagcacgtgt cactaattga agtgtcacca   1920
ataacattgt cgttattccc accattgcca ccaataagat ctccgttctt gccaccaata   1980
ccaccaataa cattgtcacc aatgacattg gcaccaataa cattgacacc aacaggtaca   2040
ccaatcgagg aaccaataga tccaccaacc gagaaaccaa cagatccacc aactgaggta   2100
ccaacactgc cttgaatccc aaagctacca acaatcccac catcttagcc taagcctatc   2160
actgttcttc cacaagttcc cagcaatagc ttgccttcca ttcctttcat gtctccatct   2220
ccacctccac ctccacctcc atccagctat tgaagacaat ttgattccta attagtatca   2280
catatattac tgagaatgaa ctctgtcatc acattctcta tgatgttatt tcatgaaata   2340
agaatgtagt ttcatttac attttacata tataataaag tgtggtgttt ttttaagtt   2400 attaaattat taaaattata tatccaaaaa tataaacatg attaaatgtt atacaatcat   2460
ttataaaggt attataattg atgctatcaa ctccaacata gttatacttc aggaaaaaaa   2520
aacataacat aatcacttgc caatgaatga tgtgattatt ttaggtataa ttgcaaaaaa   2580
atcctcaacg tttggggact tttggttttg tgcctttgac cttttttta ttgacaccct   2640 caacattata attttttttc agaaattagc ctaattttaa caataaatgt gagttaaccg   2700
ttaatcaagc gccgatcaac gaaataagtc tatgtggcat accacataag cacgatgaca   2760
tcatctaaaa aattgtttaa caatttttt ttttcatttt gtttccttct ttcttcttct   2820
ctctttctct cttcctgcta ttacag                                       2846
```

<210> SEQ ID NO 16
<211> LENGTH: 64
<212> TYPE: DNA
<213> ORGANISM: Artificial Sequence
<220> FEATURE:
<223> OTHER INFORMATION: primer gwSCWPRP_F

<400> SEQUENCE: 16

```
ggggacaagt ttgtacaaaa aagcaggcta tagtatgaga tgatctattg attctatatt    60
ctta                                                                 64
```

<210> SEQ ID NO 17
<211> LENGTH: 63
<212> TYPE: DNA
<213> ORGANISM: Artificial Sequence
<220> FEATURE:
<223> OTHER INFORMATION: primer gwSCWPRP_R

<400> SEQUENCE: 17

```
gggaccactt tgtacaagaa agctgggtat tttttggag agatgatcta aagattgaag     60
att                                                                  63
```

<210> SEQ ID NO 18
<211> LENGTH: 21
<212> TYPE: DNA
<213> ORGANISM: Artificial Sequence
<220> FEATURE:
<223> OTHER INFORMATION: primer GUSRev

<400> SEQUENCE: 18

```
tccagactga atgcccacag g                                              21
```

<210> SEQ ID NO 19
<211> LENGTH: 2831
<212> TYPE: DNA
<213> ORGANISM: Neurospora crassa

<400> SEQUENCE: 19

```
agtccagaat cagcaaccgg ttatcgagtt ccgccacaag gacggtacga gccttcagaa    60
atcgatgtca tgccaggcca gggacaccgg gatcgagtta cggaaatgcg aggcgaccgc   120
ttccctcggc accagcgcct ttacactaca atagcccaag tcgcgcagcg agtcattatc   180
cacggtacca tggaggttat gcggacgacg tgacagttag catgggaccg gacgacgatc   240
gtacagatat ctttggcccc gaaaccgatc tcagcgaaac gcgccacctc aacgacgcat   300
acgggtttcg gtcatcccag atcaccctca gcgaagatcc ccacggcacc cacgcgcgtt   360 cccgtacga cgacgaagac gatgtgagca ccacttattc ctccaacacg ggcaccagcg   420
cttcaggtgt cgacaagttc gagcattacg gtcccattcc ggaggaaggc aagcacgagc   480
ggcgcggcgt cgaccacca cagatgtcga ggaaggaagt ccagctcatc aacgcgaac    540 tcgttctcga gtgcaagatt ccgactatat tgtattcgtt tttgcccagg agagacgaag   600
tggagtttac gcacatgcgg tacacagccg tcacttgtga ccctgatgac tttgttgcca   660
ggggttacaa gttgcgccag aatatcggtc gtaccgccag ggagacggag ctgttcatct   720
gcgtgaccat gtacaacgag gacgagttcg gattcacacg gactatgcac gcagtgatga   780
agaacatttc gcattttgt tcccgaaaca gagtaggac gtgggagcg atgggtggc      840 agaagattgt ggtctgtgtg gtttcggatg gacgagagat cattcacccc cggaccttgg   900
```

```
acgccctcgc agccatgggc gtttaccagc acggtatcgc caagaacttt gtcaaccaga    960
aggcggtgca ggcccacgtt tacgagtaca cgacacaagt gtctctggac agcgacctca   1020
agttcaaggg cgccgagaag ggcatcgtgc cctgccagat gattttttgc ttgaaggaga   1080
agaaccaaaa gaaactcaac tcgcatagat ggttcttcaa cgcctttggc aaagccttga   1140
acccgaatgt gtgtatcctc ctagacgtcg gcacccgccc cggcggcaca agtctctacc   1200
atctctggaa agccttcgac acggattcca acgtggcggg ggcctgcggg gaaatcaaag   1260
cgatgaaggg gcggtttggc gggaatttgc tcaaccctct ggtggctagt cagaactttg   1320
agtacaagat gagcaatatt ctggacaaac cgttggagtc ggtgtttggg tacatcacgg   1380
tgttgccggg cgccttgtcg gcgtatcggt accatgcgct gcagaacgat gagacgggcc   1440
atgggccgtt gagtcagtat ttcaagggcg agacgctcca tgggcagcac gcggatgtgt   1500
ttacggcgaa catgtacttg gccgaggacc gaattctgtg ttgggagttg gtggccaaga   1560
ggggtgagag gtgggtgttg aagtatgtga aggggtgtac gggtgagacg gatgtgcctg   1620
acaccgtccc ggaattcgtc tcgcaacgtc gtcgttggct caacggtgcc ttcttcgccg   1680
ccgtctactc cctcgtccac tttcgacaaa tctggaaaac cgaccacacc tttatgcgca   1740
aagcccttct ccacgtcgaa ttcctctacc acctcctgca actcctcttc acctacttct   1800
ccctggccaa cttctacctc gccttctact ttatcgccgg cggactcgcc gatccccacg   1860
tcgaccctt taactcggac ggccacgtcg cgcgcatcat cttcaacatc ctccgctacg   1920
tctgcgtcct gctgatctgc acacaattca tcttgtccct cggcaaccgt ccgcagggtg   1980
ccaaaagaat gtatctcgca tccatgatca tctacgccgt catcatggtg tacaccacct   2040
tcgccaccat cttcatcgtc gtgcgacaaa tccaaccctc tcaaaaatcc gacgacaagc   2100
ccgacctcga actcggcaac aacgtcttca ccaacctgat cgtctccgtg ctagtaccc   2160
tcgggctcta cttcgtcatg tccttttctct atctcgaccc ctggcacatg ttcacctcgg   2220
ccatccagta ctttgtcctg ctgccttcct acatctgcac gctccagatc tacgccttt    2280
gcaacaccca cgacgtcaca tggggcacca aaggcgacaa cgtgatgcgc accgatctcg   2340
gaggcgccat tggcaaggga agcaccgtcg aactggaaat gccttcggac caactcgaca   2400
tcgactcggg atacgacgaa tgtctacgaa atctccggga tcgcgtcatg gtccctgccg   2460
ttcccgtgtc cgaggaccag ctgcagcagg attactacaa gtcggtgcgc acgtacatgg   2520
tggtgtcgtg gatggtggcc aacgcgacgc tggccatggc ggtgtcggaa gcgtatggcg   2580
attcggaaat tggggataat ttttacttgc ggtttatcct gtgggcggtg gcggccctgg   2640
cgctgtttag agcgttgggg tcgacgacgt ttgcggcgat taatctggtg agtgctctcg   2700
tggagggcag ggtcaggctg aggttgaata tgaaagggtt taggtggatt aaggagaagt   2760
ggggggatgc ggatgtgaag ggcaagtttg agggggtggg ggatcgggcg aggggggttgg   2820
cgaggcggtg a                                                       2831
```

<210> SEQ ID NO 20
<211> LENGTH: 105
<212> TYPE: DNA
<213> ORGANISM: Arabidopsis thaliana

<400> SEQUENCE: 20

```
atgagtaaac ggaatccgaa gattctgaag attttttctgt atatgttact tctcaactct    60
ctcttttctca tcatctactt cgttttttcac tcatcgtcgt tttca                 105
```

```
<210> SEQ ID NO 21
<211> LENGTH: 1338
<212> TYPE: DNA
<213> ORGANISM: Artificial Sequence
<220> FEATURE:
<223> OTHER INFORMATION: (double mutant of the 5-enol-pyruvylshikimate-
      3-phosphate synthase gene of Zea mays

<400> SEQUENCE: 21
atggccggcg ccgaggagat cgtgctgcag cccatcaagg agatctccgg caccgtcaag      60
ctgccggggt ccaagtcgct ttccaaccgg atcctcctac tcgccgccct gtccgagggg     120
acaacagtgg ttgataacct gctgaacagt gaggatgtcc actacatgct cggggccttg     180
aggactcttg gtctctctgt cgaagcggac aaagctgcca aaagagctgt agttgttggc     240
tgtggtggaa agttcccagt tgaggatgct aagaggaag tgcagctctt cttggggaat      300
gctggaatcg caatgcggtc cttgacagca gctgttactg ctgctggtgg aaatgcaact     360
tacgtgcttg atggagtacc aagaatgagg gagagaccca ttggcgactt ggttgtcgga     420
ttgaagcagc ttggtgcaga tgttgattgt ttccttggca ctgactgccc acctgttcgt     480
gtcaatggaa tcggagggct acctggtggc aaggtcaagc tgtctggctc catcagcagt     540
cagtacttga gtgccttgct gatggctgct cctttggctc ttggggatgt ggagattgaa     600
atcattgata aattaatctc cattccgtac gtcgaaatga cattgagatt gatggagcgt     660
tttggtgtga agcagagca ttctgatagc tgggacagat tctacattaa gggaggtcaa      720
aaatacaagt cccctaaaaa tgcctatgtt gaaggtgatg cctcaagcgc aagctatttc     780
ttggctggtg ctgcaattac tggagggact gtgactgtgg aaggttgtgg caccaccagt     840
ttgcagggtg atgtgaagtt tgctgaggta ctggagatga tgggagcgaa ggttacatgg     900
accgagacta gcgtaactgt tactggccca ccgcgggagc catttgggag gaaacacctc     960
aaggcgattg atgtcaacat gaacaagatg cctgatgtcg ccatgactct tgctgtggtt    1020
gccctctttg ccgatggccc cacagccatc agagacgtgg cttcctggag agtaaaggag    1080
accgagagga tggttgcgat ccggacggag ctaaccaagc tgggagcatc tgttgaggaa    1140
gggccggact actgcatcat cacgccgccg gagaagctga acgtgacggc gatcgacacg    1200
tacgacgacc acaggatggc gatggctttc tcccttgccg cctgtgccga ggtccccgtc    1260
accatccggg accctgggtg cacccggaag accttccccg actacttcga tgtgctgagc    1320
actttcgtca agaattaa                                                  1338

<210> SEQ ID NO 22
<211> LENGTH: 552
<212> TYPE: DNA
<213> ORGANISM: Streptomyces hygroscopicus

<400> SEQUENCE: 22
atggacccag aacgacgccc ggccgacatc cgccgtgcca ccgaggcgga catgccggcg      60
gtctgcacca tcgtcaacca ctacatcgag acaagcacgg tcaacttccg taccgagccg     120
caggaaccgc aggagtggac ggacgacctc gtccgtctgc gggagcgcta ccctggctc      180
gtcgccgagg tggacggcga ggtcgccggc atcgcctacg cgggcccctg gaaggcacgc     240
aacgcctacg actggacggc cgagtcgacc gtgtacgtct cccccgcca ccagcggacg      300
ggactgggct ccacgctcta caccaccctg ctgaagtccc tggaggcaca gggcttcaag     360
agcgtggtc ctgtcatcgg gctgcccaac gacccgagcg tgcgcatgca cgaggcgctc      420
ggatatgccc ccgcggcat gctgcggg cgccggcttca agcacgggaa ctggcatgac     480
```

```
gtgggtttct ggcagctgga cttcagcctg ccggtaccgc cccgtccggt cctgcccgtc    540
accgagatct ga                                                        552

<210> SEQ ID NO 23
<211> LENGTH: 1830
<212> TYPE: DNA
<213> ORGANISM: Escherichia coli

<400> SEQUENCE: 23
atgtgcggaa ttgttggtgc tatcgcccaa agagacgttg ctgagatttt gttagagggt     60
ctgcgaaggc tagagtatag aggatatgac tccgctggtc tggctgtcgt tgatgctgag    120
ggtcatatga caaggctaag aaggttagga aaggttcaga tgcttgctca ggcagctgag    180
gaacatccat tgcatggagg tactggtatt gcacatacca ggtgggctac tcatggggag    240
ccatcagaag ttaatgctca tccacatgtg agtgagcata tcgttgtagt tcacaatggg    300
ataattgaaa accacgaacc attgagggaa gagttaaagg caagaggata tacttttgtg    360
agtgagactg acactgaggt tattgcacat ttagtgaact gggaactcaa acagggggc     420 acattgcgtg aggctgtgtt aagagctatt cctcaactta gaggtgcata cggtactgtt    480
attatggatt caagacaccc agatactctc cttgcagcta gatcaggtag tcccttggtc    540
ataggacttg gaatgggtga aaattttatc gctagcgacc aattggcctt attgccagtt    600
acaagacgat ttattttcct tgaagagggc gatattgctg agattactag aaggtctgtg    660
aacatctttg ataagactgg cgctgaggtt aaacgtcagg atatcgagtc taaccttcaa    720
tacgatgctg gtgataaagg aatttacagg cattatatgc aaaaggaaat ttatgaacaa    780
ccaaatgcta tcaaaaacac acttactggc cgtatttctc atggacaggt cgatttaagc    840
gagcttggtc ctaatgcaga cgaactgcta tcaaaagttg agcacataca gatactggca    900
tgcggaacta gttataattc aggaatggtg tctagatact ggttcgaaag cttggcaggt    960
ataccttgtg atgtagagat cgcttctgag tttaggtata gaaagtctgc tgtgcgtaga   1020
aattcattaa tgattacatt atctcaatcc ggagaaacag cagatacact ggctggattg   1080
aggctttcta aggaactcgg atatctgggt tcacttgcta tttgtaatgt accaggttcc   1140
tcattggttc gtgaatcaga tctagcactt atgacaaatg caggaactga ataggtgtg    1200 gcaagtacca aggcttttcac aacccaactg accgtacttt taatgttggt agcaaaactc   1260
agtcgattaa aggggctaga tgcatctatc gaacatgata ttgttcacgg gcttcaagct   1320
ctcccttcaa gaattgaaca aatgctttca caagataaga gaatagaggc attggctgaa   1380 gattttccg acaaacatca cgcattgttt cttggacgtg gcgatcaata tccaattgca   1440
ttggaaggag ctttgaagtt gaaagaaata agttacattc acgcagaagc atatgcagct   1500
ggagaactca agcatggtcc tttggcactc atcgacgctg acatgcccgt gatcgtagtg   1560
gctcctaata acgaactgct cgaaaagctt aaatcaaata tcgaagaggt tcgagctaga   1620
ggaggtcagc tttacgtttt cgctgaacaa gatgctggat tcgtgtcaag cgataatatg   1680
catataattg aaatgcctca cgttgaagaa gtgattgcac ctatatttta tacagtccca   1740
ttgcaacttc tagcttacca tgttgcactt attaaaggaa ctgatgttga tcagcctaga   1800
aacctagcaa aatctgtaac agtcgaataa                                    1830
```